(12) United States Patent (10) Patent No.: US 9,354,200 B1
Caulfield (45) Date of Patent: May 31, 2016

(54) DETECTION APPARATUS FOR DIFFERENTIAL-CHARGED PARTICLE MOBILITY ANALYZER

(75) Inventor: Michael P. Caulfield, San Clemente, CA (US)

(73) Assignee: QUEST DIAGNOSTICS INVESTMENTS INCORPORATED, San Juan Capistrano, CA (US)

( * ) Notice: Subject to any disclaimer, the term of this patent is extended or adjusted under 35 U.S.C. 154(b) by 0 days.

(21) Appl. No.: 12/537,191

(22) Filed: Aug. 6, 2009

Related U.S. Application Data

(60) Provisional application No. 61/087,148, filed on Aug. 7, 2008.

(51) Int. Cl.
| | |
|---|---|
| *G01N 27/62* | (2006.01) |
| *G01N 31/00* | (2006.01) |
| *A61K 9/127* | (2006.01) |
| *C07K 14/775* | (2006.01) |

(52) U.S. Cl.
CPC ............ *G01N 27/624* (2013.01); *A61K 9/1275* (2013.01); *C07K 14/775* (2013.01); *G01N 31/00* (2013.01)

(58) Field of Classification Search
None
See application file for complete search history.

(56) References Cited

U.S. PATENT DOCUMENTS

| | | | |
|---|---|---|---|
| 1,825,661 A | 10/1931 | Gull | |
| 4,678,566 A | 7/1987 | Watanabe et al. | |
| 4,933,844 A | 6/1990 | Otvos | |
| 5,076,097 A | 12/1991 | Zarrin et al. | |
| 5,247,842 A | 9/1993 | Kaufman et al. | |
| 5,343,389 A | 8/1994 | Otvos | |
| 5,460,974 A | 10/1995 | Kozak et al. | |
| 5,561,515 A | 10/1996 | Hairston et al. | |
| 5,595,913 A | 1/1997 | Lawlor et al. | |
| 5,701,012 A | 12/1997 | Ho | |
| 5,756,291 A | 5/1998 | Griffin et al. | |
| 5,788,166 A | 8/1998 | Valaskovic et al. | |
| 5,856,196 A | 1/1999 | Alvarez et al. | |
| 5,895,922 A | 4/1999 | Ho | |
| 5,925,229 A | 7/1999 | Krauss et al. | |
| 5,932,080 A * | 8/1999 | Likuski | 204/451 |
| 5,999,250 A | 12/1999 | Hairston et al. | |
| 6,020,208 A | 2/2000 | Hutchens et al. | |
| 6,107,045 A | 8/2000 | Koren et al. | |
| 6,126,835 A | 10/2000 | Barbera-Guillem et al. | |
| 6,145,391 A | 11/2000 | Pui et al. | |

(Continued)

FOREIGN PATENT DOCUMENTS

| | | |
|---|---|---|
| EP | 0 546 916 | 6/1993 |
| EP | 0 627 627 | 12/1994 |

(Continued)

OTHER PUBLICATIONS

Hildebrandt et al "Superparamagentic ion ocise nanoparticles functionalized with peptides by electrostatic interactions" ARKIVOC, 2007, 79-90.*

(Continued)

*Primary Examiner* — Alexander Kim
(74) *Attorney, Agent, or Firm* — Foley & Lardner

(57) ABSTRACT

The present invention provides devices and methods for identification and/or quantitation of particles through detection of fluorescence labeled particles in an apparatus for differential charged particle mobility analysis and fluorescence detection.

12 Claims, 8 Drawing Sheets

(56) References Cited

U.S. PATENT DOCUMENTS

| | | | |
|---|---|---|---|
| 6,248,545 | B1 | 6/2001 | Kondo et al. |
| 6,267,579 | B1 | 7/2001 | Li et al. |
| 6,469,297 | B1 | 10/2002 | Kato et al. |
| 6,485,686 | B1 | 11/2002 | Wick |
| 6,491,872 | B1 | 12/2002 | Wick |
| 6,716,994 | B1 * | 4/2004 | Menchen et al. ............ 548/455 |
| 6,753,185 | B2 | 6/2004 | MacFarlane et al. |
| 7,075,066 | B2 | 7/2006 | Bailey et al. |
| 7,259,018 | B2 | 8/2007 | Benner et al. |
| 8,247,235 | B2 | 8/2012 | Caulfield et al. |
| 2002/0098597 | A1 * | 7/2002 | Koren et al. ................. 436/530 |
| 2003/0066969 | A1 | 4/2003 | De La Mora |
| 2003/0124743 | A1 | 7/2003 | Kundu |
| 2003/0136680 | A1 | 7/2003 | Benner et al. |
| 2003/0234356 | A1 | 12/2003 | Konermann et al. |
| 2004/0029293 | A1 | 2/2004 | Nugent et al. |
| 2004/0119009 | A1 | 6/2004 | Hanold et al. |
| 2004/0137542 | A1 | 7/2004 | Petyaev |
| 2005/0023455 | A1 | 2/2005 | Bailey et al. |
| 2005/0042695 | A1 | 2/2005 | Meares et al. |
| 2005/0061722 | A1 | 3/2005 | Takao et al. |
| 2007/0048795 | A1 | 3/2007 | Fang et al. |
| 2007/0090026 | A1 * | 4/2007 | Han et al. ........................ 209/2 |
| 2008/0302666 | A1 * | 12/2008 | Benner et al. ................. 204/645 |
| 2008/0305549 | A1 * | 12/2008 | Caulfield et al. ............... 436/71 |
| 2009/0132443 | A1 * | 5/2009 | Mueller et al. ................. 706/12 |
| 2009/0136937 | A1 * | 5/2009 | Coleman et al. ................. 435/6 |

FOREIGN PATENT DOCUMENTS

| | | |
|---|---|---|
| EP | 1 045 247 | 10/2000 |
| JP | 09-072891 | 3/1997 |
| JP | 2001-124780 A | 5/2001 |
| JP | 2001-527090 T | 12/2001 |
| WO | WO-93/17776 | 9/1993 |
| WO | WO-99/17096 | 4/1999 |
| WO | WO-00/51054 | 8/2000 |
| WO | WO-00/65366 | 11/2000 |
| WO | WO-03/042704 | 5/2003 |
| WO | WO-2004/014942 | 2/2004 |
| WO | WO-2007/004687 | 1/2007 |
| WO | WO-2008/154422 | 12/2008 |

OTHER PUBLICATIONS

Atherotech, Inc., Test Benefits—VAP/CAD Lipoprotein Risk Assessment Test, http://home.socal.rr.com/asylem/test_ben.htm, Artherotech, Inc., USA, p. 1-3, 2001.

Bacher et al, Charge-reduced nano electrospray ionization combined with differential mobility analysis of peptides, proteins, glycoproteins, noncovalent protein complexes and viruses, Journal of Mass Spectrometry, 36(9):1038-1052, Sep. 2001.

Barbagallo et al, Influence of ApoE content on receptor binding of large buoyant LDL in subjects with different DLD subclass phenotypes, J. Amer. Heart Association, p. 466-472, 1998.

Bell et al, [LJ.09] The dynamics of a steady Taylor cone electrospray, BAPSDFD98—Abstracts, American Physical Society, USA, Nov. 24, 1998.

Benner et al, Investigating Intact Viruses with Charge-Detection MS and Ion Mobility, Proc. 49th ASMS Conf. on Mass Spectrometry and Allied Topics, ASMS, Chicago IL, May 27, 2001.

Berneis et al., Analysis and quantitation of biotinyfated apoB-containing lipoproteins with streptavidin-Cy3, J. Lipid Res., 43:1155-1159, 2002.

Berneis et al., Metabolic origins and clinical significance of LDL heterogeneity, J, Lipid Res., 43:1363-1379, 2002.

Bundy et al, A novel Method for the Analysis of Complex Biological Protein Mixtures Using Electrospray Ionization Mass Spectrometry Combined with Ion/Ion Chemistry, Proc. 49th ASMS Cont. on Mass Spectrometry and Allied Topics, ASMS, Chicago IL, May 27, 2001.

Campos et al, Predominance of large LDL and reduced HDL2 cholesterol in normolipidemic men with coronary artery disease, Arteriosclerosis, Thrombosis & Vascular Biology, 15(8):1043-1048, Aug. 1995.

Communication dated Jul. 6, 2010 in related EP application 08770383.

Dreon et al, Diet-gene interactions in human lipoprotein metabolism, J. Amer. College of Nutrition, 16(4):313-324, 1997.

Dreon et al, LDL subclass patterns and lipoprotein response to a low-fat, high-carbohydrate diet in women, Arteriosclerosis, Thrombosis & Vascular Biology, 17(4):707-714, Apr. 1997.

Dreon et al, Low-density lipoprotein subclass patterns and lipoprotein response to a reduced-fat diet in men, Faseb Journal, 8(1):121-126, Jan. 1994.

Dreon et al, Reduced LDL particle size in children consuming a very-low-fat diet is related to parental LDL-subclass patterns, Am. J. Clin. Nutr., 71:1611-1616, 2000.

Dreon et al., A very low-fat diet is not associated with improved lipoprotein profiles in men with a predominance of large, low-density lipoproteins, Am. J. Clin. Nutr., 69: 411-418, 1999.

Dreon et al., Change in dietary saturated fat intake is correlated with change in mass of large low-density-lipoprotein particules in men, Am. J. Clin. Nutr., 67:828-836, 1998.

Edmonds et al, Capillary Electrophoresis-Electrospray Ionization-Mass Spectrometry, J. Chromatogr., PNL, USA, p. 21-37, 1989.

Feingold et al., The hypertriglyceridemia of acquired immunodeficiency syndrome is associated with an increased prevalence of low density lipoprotein subclass pattern B, Journal of Clinical Endocrinology & Metabolism, 76(6):1423-1427, Jun. 1993.

Friedewald et al., Estimation of the concentration of low-density lipoprotein cholesterol in plasma, without use of the preparative ultracentrifuge, Clin. Chem., 1972, 18:499-502.

Gardner et al, Association of small low-density lipoprotein particles with the incidence of coronary artery disease in men and women, Comment in: JAMA, vol. 276(11):875-881, Sep. 18, 1996.

Gray et al, Relation of LDL size to the insulin resistance syndrome and coronary heart disease in American Indians, Arteriosclerosis, Thrombosis & Vascular Biology, 17(11):2713-2720, Nov. 1997.

Haskell et al, Effects of intensive multiple risk factor reduction on coronary atherosclerosis and clinical cardiac events in men and women with coronary artery disease. The Stanford Coronary Risk Intervention Project (SCRIP), Circulation, 89(3):975•990, Mar. 1994.

Havel et al, Genetic underpinnings of LDL size and density: a role for hepatic lipase?, Am. J. Clin. Nutr., 71:1390-1391, 2000.

Henderson et al, Intrinsic Size Parameters for Val, Ile, Leu, Gln, Thr, Phe, and Trp Residues from Ion Mobility Measurements of Polyamino Acid Ions, J. Phys. Chem. B, 103:8780•8785, 1999.

Hodis et al, Intermediate-density lipoproteins and progression of carotid arterial wall intima-media thickness, Circulation, 95(8):2022-2026, Apr. 15, 1997.

International Preliminary Report on Patentability dated Dec. 11, 2009 in related application.

International Search Report dated Aug. 20, 2008 in related application PCT/US2008/066178.

Jeyarajah et al, Radio signals give new spectrum for cholesterol lipoprotein readings, American Heart Association Journal Report—News Release, American Heart Association, USA, p. 1-3, Jul. 9, 1998.

Jeyarajah et al., Lipoprotein particle analysis by nuclear magnetic resonance spectroscopy, Clin Lab Med., 2006, 26:847-870.

Katzel et al, Persistence of low HDL-C levels after weight reduction in older men with small LDL particles, Arteriosclerosis, Thrombosis & Vascular Biology, 15(3):299-305, Mar. 1995.

Krauss et al, Detection and quantitation of LDL subfractions, Current Opinion in Lipidology, Current Science Ltd., 3:377-383, 1992.

Krauss et al, Lipoprotein subclasses in genetic studies: the Berkeley data set, Genetic Epidemiology, 10(6):523-528, 1993.

Krauss et al, Low-density-lipoprotein subclasses and response to a low-fat diet in healthy men, American Journal of Clinical Nutrition, 62(2):4785-4875, Aug. 1995.

Krauss et al., Atherogenic lipoprotein phenotype and diet-gene interactions, American Society for Nutritional Science Symposium: Nutritional and Metabolic Diversity: Understanding the Basis of Biologic Variance in the Obesity/Diabetes/Cardiovascular Disease Connection, p. 340S-343S, 2001.

(56) References Cited

OTHER PUBLICATIONS

Krauss, R.M., Dietary and genetic effects on low-density lipoprotein heterogeneity, Annu. Rev. Nutr. 21:283-295, 2001.
Krauss, R.M., Is the size of low-density lipoprotein particles related to the risk of coronary heart disease?, JAMA, 287(6): 712-713, Feb. 13, 2002.
Krauss, R.M., Triglyceride-Rich Lipoproteins, LDL Particle Size, and Atherogenesis, American Assoc. of Clinical Endocrinologists Ninth Annual Meeting and Clinical Congress, Amer. Assoc. Clinical Endocrinologists, May 3, 2000.
Kulkarni et al., Quantification of cholesterol in all lipoprotein classes by the VAP-II method, J. Lip. Res., 1994, 35:159-168.
Legro et al., Alterations in low-density lipoprotein and high-density lipoprotein subclasses among Hispanic women with polycystic ovary syndrome: influence of insulin and genetic factors, Fertility and Sterility, 72(6):990-995, Dec. 1999.
Lindgren et al, Chapter 5—The Isolation and Quantitative Analysis of Serum Lipoproteins, Blood Lipids and Lipoproteins: Quantitation Composition and Metabolism, 1992, p. 181-274.
Mack et al, Lipoprotein subclasses in the Monitored Atherosclerosis Regression Study (MARS), Treatment effects and relation to coronary angiographic progression, Arteriosclerosis, Thrombosis & Vascular Biology, 16(5):697-704, 1996.
Muniz et al, A New Tool for the Automated Analysis of LDL Subfraction Patterns Generated by the Lipoprint LDL System, www.4qc.com, Quantimetrix Corporation, USA, p. 1-11, 2001.
New Objective, Inc., Bring Electrospray Into Focus, LC-MS Nano-ESI Proteomics, New Objective, Inc. (www.newobjective.com), USA, 2001.
New Objective, Inc., Product Catalog: Fused Silica Pica Tips, Products (www.newobjective.com), New Objective, Inc., USA, 2001.
New Objective, Inc., What is Electrospray?, Products (www.newobjective.com), New Objective, Inc., USA, 2001.
New Objective, Inc., What New Objective Can Do for You, www.newobjective.com, New Objective, Inc., Cambridge, MA. No date available.
Quantimetrix Corporation, Lipoprint System for LDL Subfraction, Lipoprint Technical—What's New (www.4qc.com), Quantimetrix Corporation, USA, p. 1, 2001.
Roche, Quick spin protein columns: G-25 sephadex (fine) columns for protein desalting and buffer exchange, Version Jan. 2, 2002.
Sigma, R2882 Reactive Green 19-Agarose, Saline suspension.
Stampfer et al, A prospective study of triglyceride level, low-density lipoprotein particle diameter, and risk of myocardial infarction, Comment in: JAMA, 276(11):882-888, Sep. 18, 1996.
Superko et al, Association of lipoprotein subclass distribution with use of selective and non-selective beta-blocker medications in patients with coronary heart disease, Atherosclerosis, 101(1):1-8, Jun. 1993.
Superko et al, Effect of Fluvastatin on Low-density lipoprotein peak particle diameter, Amer. J. of Cardiology, 80:78-81, Jul. 1, 1997.
Superko et al, Garlic powder, effect on plasma lipids, postprandial lipemia, low-density lipoprotein particle size, high-density lipoprotein subclass distribution and lipoprotein(a), J. Am. College of Cardiology, 35(2):321-326, 2000.
Tribble et al., Enhanced oxidative susceptibility and reduced antioxidant content of metabolic precursors of small, dense low-density lipoproteins, Amer. J. of Medicine, 110:103-110, 2001.
TSI Incorporated, Correlation of EM Diameter with Molecular Weight, GEMMA Example—EM Diameter vs. Molecular Weight (www.tsi.com), TSI Incorporated, Particle Instrumentation Division, USA, 1999.
TSI Incorporated, GEMMA Method for Macromolecule/Nanoparticle Analysis, GEMMA Method Product Page (www.tsi.com), TSI Incorporated, Particle Instrument Division, USA, 1999.
TSI Incorporated, Model 3080-Series Electrostatic Clasifiers, TSI Product Info. Sheets (www.tsi.com),TSI Incorporated, USA, 1999.
TSI Incorporated, Model 3312 Ultraviolet Aerodynamic Particle Sizer Spectrometer, Preliminary Product Information (www.tsi.com), TSI Incorporated, USA, 1997.
TSI Incorporated, Model 3313 Fluorescence Aerodynamic Particle Sizer Sensor, 2002, 4 pgs.
TSI Incorporated, Model 3480 Electrospray Aerosol Generator, 3480 Advance Product Information (www. tsi.com), TSI Incorporated, Particle Instrument Division, USA, 1999.
TSI Incorporated, Model 3980 GEMMA Macromolecule Analyzer; TSI Advance Product Information (www.tsi.com), TSI Incorporated, USA, 2000.
TSI Incorporated, Protein Mixture, GEMMA Example—Protein Mixture (www.tsi.com), TSI Incorporated, Particle Instrument Division, USA, 1999.
US Office Action dated May 19, 2010 in related U.S. Appl. No. 11/760,700.
US Office Action dated Jun. 29, 2010 in related U.S. Appl. No. 11/760,672.
US Office Action dated Sep. 1, 2009 in related U.S. Appl. No. 11/760,700.
Waugh et al, Rapid method for determining cholesteryl ester transitions of apoB-containing lipoproteins, Journal of Lipid Research, 23:201-204, 1982.
Williams et al, Associations of age, adiposity, alcohol intake, menstrual status, and estrogen therapy with high-density lipoprotein subclasses, Arteriosclerosis and Thrombosis, 13(11):1654-1661, Nov. 1993.
Williams et al, Effects of dietary fat on high-density-lipoprotein subclasses are influenced by both apolipoprotein E isoforms and low-density-lipoprotein subclass patterns, American Journal of Clinical Nutrition, 61(6):1234-1240, Jun. 1995.
Williams et al, The associations of high-density lipoprotein subclasses with insulin and glucose levels, physical activity, resting heart rate, and regional adiposity in men with coronary artery disease . . . , Metabolism: Clinical & Experimental, 44(1)106-114, Jan. 1995.
Williams et al, Variability of plasma HDL subclass concentrations in men and women over time, Arteriosclerosis, Thrombosis & Vascular Biology, 17(4):702-706, Apr. 1997.
Williams et al., Low-fat diets, lipoprotein subclasses, and heat disease risk, Am. J. Clin. Nutr., 70:949-950, 1999.
Yang et al., Multilectin affinity chromatography for characterization of multiple glycoprotein biomarker candidates in serum from breast cancer patients, Clinical Chemistry, 52(2):1-9, 2006.
First Office Action issued in Chinese Patent Application No. 200880101850.3 dated Jul. 3, 2012 (17 pages)—English summary provided by Foreign Associate included.
Communication pursuant to Article 94(3) EPC dated Apr. 11, 2012 in EP application 08770383.1.
"Reactive Dye Affinity Chromatography Matrices" Sigma Product Information, Jan. 10, 2000, XP055050205, 6 pages.
Davies, et al., "Rapid Separation of LDL Subclasses by Iodixanol Gradient Ultracentrifugation", Clinical Chemistry, 2003, vol. 49, No. 11, 1865-1872.
EPO Communication issued in application EP 08770383.1 dated Jan. 28, 2013.
Final Office Action issued for U.S. Appl. No. 13/589,404 dated Apr. 25, 2013.
Office Action issued in Chinese Patent Application No. 200880101850.3 dated Mar. 14, 2013.
Office Action issued in Japanese Patent Application No. 2010-511380 dated Mar. 12, 2013.
Notice of Allowance dated Apr. 5, 2012 for U.S. Appl. No. 11/760,672.
Non-Final Office Action in U.S. Appl. No. 13/340,547 dtd Oct. 8, 2013.
Notice of Allowance in U.S. Appl. No. 13/589,404 dtd Dec. 12, 2013.
Office Action in CN application No. 200880101850.3 dtd Nov. 28, 2013 (English translation).
Warnick, G.R., et al., Dextran Sulfate-Mg2+ Precipitation Procedure for Quantitation of High-Density-Lipoprotein Cholesterol, Clin. Chem., 28, pp. 1379-1388, (1982).
Burstein, et al., "Rapid Method for the Isolation of Two Purified Subfractions of High Density Lipoproteins by Differential Dextran Sulfate-Magnesium Chloride Precipitation," Biochimie, Masson, Paris, FR, vol. 71, No. 6, 1989, pp. 741-746.

(56) References Cited

OTHER PUBLICATIONS

Gross, et al., "Isolation of Lipoprotein (a) Using the Regenerate of a Dextran Sulfate Cellulose LDL Apheresis System," Protein Expression and Purification, Academic Press, San Diego, CA, vol. 5, No. 2, 1994, pp. 112-117.
Hennessy, et al., "Isolation of Subpopulations of High Density Lipoproteins: Three Particle Species Containing apoE and Two Species Devoid of apoE that Have Affinity for Heparin," Journal of Lipid Research, vol. 38, No. 9, 1997, pp. 1859-1868.
Kaddis, et al., "Sizing Large Proteins and Protein Complexes by Electrospray Ionization Mass Spectrometry and Ion Mobility," Journal of the American Society for Mass Spectrometry, Elsevier Science Inc, US, vol. 18, No. 7, 2007, pp. 1206-1216.
Mulholland, et al., "Measurement of 100 nm and 60 nm Particle Standards by Differential Mobility Analysis," Journal of Research of the National Institute of Standards and Technology, vol. 111, No. 4, 2006, pp. 257-312.
Notice of Allowance in U.S. Appl. No. 13/589,404 dtd Sep. 4, 2013.
Partial European Search Report in EP application No. 13169486.1 dtd Aug. 14, 2013.
Partial European Search Report in EP application No. 13169517.3 dtd Aug. 16, 2013.
Sjoblom, et al., "Determination of HDL2 Cholesterol by Precipitation with Dextran Sulfate and Magnesium Chloride: Establishing Optimal Conditions for Rat Plasma," Lipids, Springer-Verlag, Berlin/Heidelberg, vol. 24, No. 6, 1989, pp. 532-534.
Talameh, et al., "Measurement of Total HDL, HDL2 and HDL3 by Dextran Sulfate -MgCl2 Precipitation Technique in Human Serum," Clinica Chimica Acta, Elsevier BV, Amsterdam, NL, vol. 158, No. 1, 1986, pp. 33-41.
Vallance, et al., "Precipitation Procedures Used to Isolate High Density Lipoprotein with Particular Reference to Effects on Apo A-I-Only Particles and Lipoprotein(a)," Clinica Chimica Acta, Elsevier BV, Amsterdam, NL, vol. 229, No. 1-2, 1994, pp. 77-85.
Altintas, et al, Efficient removal of albumin from human serum by monosize dye-affinity beads, (2006), J Chromatography B, 832(2):216-223.
Amthauer, et al, Interaction of cibacron blue and anilinonaphthalenesulphonate with lipoproteins provides a new mean for simple isolation of these plasma proteins, (1988), Biochem Biophys Res Comm, 154(2):752-757.
Axis-Shield PoC AA: Optiprep—product description, (2003), XP002598992, retrieved from URL:http://www.freewebs.com/eldril123/packageinsert/optiprep.pdf, retrieved on Aug. 31, 2010.
Caulfield, et al, Direct determination of lipoprotein particle sizes and concentrations by ion mobility analysis, (2008), Clin Chem, 54(8):1307-1316.
Davies, et al., Rapid separation of LDL subclasses by iodixanol gradient ultracentrifugation, (2003), Clin Chem, 49(11):1865-1872.
Extended European Search Report dated Sep. 20, 2010 in EP application 08770383.
Gardner, et al, Separation of bovine plasma lipoproteins by a rapid ultracentrifugation method, (2003), J Comp Path, 128(1):15-23.
Graham, et al., A novel method for the rapid separation of plasma lipoproteins using self-generating gradient of iodixanol, (1996), Atherosclerosis, 124(1):125-135.
Griffin, et al, Rapid isolation of low density lipoprotein LDL subfractions from plasma by density gradient ultracentrifugation, (1990), Atherosclerosis, 83(1):59-68.
Hallberg, et al., Lipoprotein fractionation in deuterium oxide gradients, (1994), J Lipid Research, 35(1):1-9.
US Office Action dated Jul. 11, 2011 in U.S. Appl. No. 11/760,672.
US Office Action dated Sep. 22, 2010 in U.S. Appl. No. 11/760,672.
US Office Action dated on Oct. 8, 2010 in U.S. Appl. No. 11/760,700.
Patent Examination Report No. 1 Issued in Australian Patent Application No. 2008261868 dated Mar. 8, 2013.
Non-final office action dated Dec. 7, 2011 for U.S. Appl. No. 11/760,672.
Non-Final Office Action for U.S. Appl. No. 13/589,404 dated Nov. 29, 2012.

Notice of Reasons for Rejection issued in Japanese Application No. 2010-511380 dtd Jan. 7, 2014 (includes English translation—5 page).
Nauck, et al., "New immunoseparation-based homogeneous assay for HDL-cholesterol compared with three homogeneous and two heterogeneous methods for HDL-cholesterol," Clinical Chemistry, vol. 44:7, 1998, pp. 1443-1451.
Non-Final Office Action in U.S. Appl. No. 14/226,089 dtd Jun. 26, 2014 (14 pages).
Final Office Action in U.S. Appl. No. 13/340,547 dtd Jul. 3, 2014 (24 pages).
Gibson, et al., "Precipitation of apo E-containing lipoproteins by precipitation reagents for apolipoprotein B," Clin. Chem.(1984), vol. 30(11), pp. 1784-1788.
Gold Biotechnology, "Plain & Crosslinked Agarose Beads," accessed at https://www.goldbio.com/documents/1016/Agarose beads—General Information.pdf on Jul. 29, 2014. (3 pages).
Merki, et al., "Antisense Oligonucleotide Directed to human Apolipoprottein B-100 Reduces Lipoprotein(a) Levels and Oxidized Phospholipids on Human Apolipoprotein B-100 Particles in Lipoprotein(a) Transgenic Mice," Circulation (2008), vol. 11825, pp. 743-753.
Nauck, et al., "New immunoseparation-based homogeneous assay for HDL-cholesterol compared with three homogeneous and two heterogeneous methods for HDL-cholesterol," Clin Chem. (1998) vol. 44(7), pp. 1443-1451.
Nierman, et al., "Enhanced Conversion of Triglyceride-Rich Lipoproteins and Increased Low-Density Lipoprotein Removal in LPLS447X Carriers," Arteriosclerosis, Thrombosis, and Vascular Biology (2005), vol. 25, pp. 2410-2415.
Zhou, et al., "Preparation of uniform-sized agarose beads by microporous membrane emulsification technique," Journal of Colloid and Interface Science (2007), vol. 311, pp. 118-127.
Notice of Allowance in U.S. Appl. No. 14/226,089 dtd Jan. 26, 2015 (9 pages).
Angal, et al., "The Effect of Matrix on the Binding of Albumin to Immobilized Cibacron Blue," Biochem. J. (1977) 167, pp. 301-303.
Bairaktari et al., Evaluation of Methods for the Measurement of Low-Density Lipoprotein Cholesterol, J Cardiovasc Pharmacol Therapeut (2005), vol. 10, pp. 45-54.
Communication Pursuant to Article 94(3) EPC in European Application No. 13169486.1 dtd Nov. 10, 2014 (5 pages).
Communication under Rule 71(3) EPC in European Application No. 08770383.1 dtd Oct. 29, 2014 (7 pages).
Esteban-Salan et al., Analytical and Clinical Evaluation of Two Homogeneous Assays for LDL-Cholesterol in Hyperlipidemic Patients., Clinical Chemistry (2000), vol. 46 No. 8 1121-1131.
Final Office Action in U.S. Appl. No. 14/226,089 dtd Oct. 8, 2014 (13 pages).
Finley et al., Cholesterol in high-density lipoprotein: use of Mg2+/dextran sulfate in its enzymic measurement, Clinical Chemistry (1978), vol. 24, pp. 931-933.
Fowkes et al., Inter-relationships of plasma fibrinogen, low-density lipoprotein cholesterol, cigarette smoking and the prevalence of cardiovascular disease., J Cardiovasc Risk. (1996), vol. 3(3), pp. 307-311.
Janado et al., Sedimentation Properties of Dextran Sulfate-Low Density Lipoprotein Complexes., Agricultural and Biological Chemistry (1967), vol. 31, pp. 802-808.
Non-Final Office Action in U.S. Appl. No. 13/340,547 dtd Jan. 14, 2015 (24 pages).
Notice of Reasons for Rejection in Japanese Application No. 2010-511380 dtd Nov. 18, 2014 (English translation included—3 pages).
Rudel et al., Characterization of Plasma Lipoproteins Separated and Purified by Agarose-Column Chromatography, Biochem. J. (1974), vol. 139, pp. 89-95.
Sera-Mag SpeedBeads Magnetic Microparticles (Oct. 2006).
Sera-Mag® Magnetic Carboxylate-Modified Microparticles (Nov. 2000).

(56) References Cited

OTHER PUBLICATIONS

Sigma-Aldrich, "Reactive Blue 4-Agarose," 2012, 2 pages.
Sigma-Aldrich, "Reactive Brown 10-Agarose," 2012, 2 pages.
Sigma-Aldrich, "Reactive Green 5-Agarose," 2012, 1 page.
Sigma-Aldrich, "Reactive Yellow 86-Agarose," 2012, 1 page.
Stec et al., Association of Fibrinogen With Cardiovascular Risk Factors and Cardiovascular Disease in the Framingham Offspring Population, Circulation (2000), vol. 102, pp. 1634-1638.
US Office Action in U.S. Appl. No. 13/340,547 dated Jul. 15, 2015 (9 pages).
US Notice of Allowance in U.S. Appl. No. 13/340,547 dated Oct. 2, 2015 (12 pages).

* cited by examiner

DETECTION APPARATUS FOR DIFFERENTIAL-CHARGED PARTICLE MOBILITY ANALYZER

CROSS-REFERENCE TO RELATED APPLICATION

This patent application claims priority to U.S. Provisional Patent Application No. 61/087,148, entitled "Detection Apparatus For Differential-Charged Particle Mobility Analyzer," filed Aug. 7, 2008, which is hereby incorporated by reference in its entirety for all purposes.

FIELD OF THE INVENTION

The present invention generally relates to the fields of particle size analysis including the analysis of biological particles including lipoproteins, nucleic acids and proteins for diagnostic purposes utilizing ion mobility measurement devices.

BACKGROUND OF THE INVENTION

The following description is provided solely to assist the understanding of the present invention. None of the references cited or information provided is admitted to be prior art to the present invention. All patents and other references cited in the specification are incorporated by reference in their entireties, including any tables and figures, to the same extent as if each reference had been incorporated by reference in its entirety individually.

Cardiovascular disease is the leading cause of death in the United States. The most commonly used and accepted methods for determining risk of future heart disease include evaluating serum levels of cholesterol and lipoproteins in light of patient demographics and current health. There are well established recommendations for cut-off values for biochemical markers for determining risk, including, for example without limitation cholesterol and lipoprotein levels. However, cholesterol and lipoprotein measurements are clearly not the sole contributors to cardiovascular disease because as many as 50% of people who are at risk for premature heart disease are currently not encompassed by the ATP III guidelines (i.e., Adult Treatment Panel III guidelines issued by the National Cholesterol Education Program and the National Heart, Lung and Blood Institute).

SUMMARY OF THE INVENTION

The present invention provides apparati and methods for detecting fluorescently labeled biological particles with a differential-charged particle mobility analysis device.

Thus, in a first aspect, the invention features an apparatus for differential-charged particle mobility analysis and fluorescence detection. The apparatus has one or more pumps, an ionizer, a differential-charged particle mobility analyzer, and a fluorescence detection system. The pump(s) transport a sample containing fluorophore labeled particles through a capillary where they are charged by the ionizer. The differential-charged particle mobility analyzer receives a sample of particles charged by the ionizer. The particles are then analyzed by differential-charged particle mobility analysis and fluorescence from the charged particles is detected.

In some embodiments, the apparatus further comprises an autosampler adapted to provide a sample for differential-charged particle mobility analysis to the one or more pumps. In some embodiments, the fluorescence detection system of the apparatus comprises one or more excitation sources and one or more fluorescence detectors. In some related embodiments, the fluorescence detection system comprises a single excitation source and a single fluorescence detector positioned on either side of a flow of the sample of charged particles. In some other related embodiments, the fluorescence detection system comprises an excitation source and multiple fluorescence detectors. In some further related embodiments, the excitation source and fluorescence detectors are arranged in an annular array positioned around a flow of the sample of charged particles.

In some embodiments, the one or more excitation sources comprise one or more laser excitation sources. In some related embodiments, a laser excitation source operates in pulse mode. In other related embodiments, the laser excitation source operates in continuous mode.

In a second aspect, the invention features method of determining the recovery of particles subjected to differential-charged particle mobility analysis. In the method, a known amount of a fluorophore labeled particle is added to a sample. The fluorophore labeled particles are then introduced to an apparatus for differential-charged particle mobility analysis and fluorescence detection. The amount of fluorophore labeled particle in the sample after differential-charged particle mobility analysis is then determined, and the amount of fluorophore labeled particles detected after differential-charged particle mobility analysis is compared to the known amount of fluorophore labeled particles in the sample prior to analysis to determine recovery. In some embodiments, the sample is a biological sample. In some embodiments, the fluorophore labeled particle is a fluorophore labeled lipoprotein, nucleic acid or protein. In other embodiments, the fluorophore labeled particle comprises a fluorophore labeled lipid. In related embodiments, the fluorophore labeled lipid is labeled with a lipophilic fluorophore. In some embodiments, the lipophilic fluorophore is selected from the group consisting of 1,1'-dioctadecyl-3,3,3',3'-tetramethylindocarbocyanine perchlorate (DiI), 3,3'-dioctadecyloxacarbocyanine perchlorate (DiO), 1,1'-dioctadecyl-3,3,3',3'-tetramethylindodicarbocyanine perchlorate (DiD), 1,1'-dioctadecyl-3,3,3',3'-tetramethylindotricarbocyanine iodide (DiR), Alexa Fluor 488 (carboxylic acid, succinimidyl ester 'mixed isomers'), and fluorescein-5-EX, succinimidyl ester; preferably DiI or Alexa Fluor 488.

In a third aspect, the invention features a method for quantitation of biological particles in a sample. In the method, the sample is contacted with a first fluorophore labeled entity that is capable of integrating into a particle of interest to generate first fluorescently labeled particles. The first fluorescently labeled particles are then introduced to an apparatus for differential-charged particle mobility analysis and fluorescence detection and the fluorescently labeled particles are quantitated in the apparatus. In some embodiments, the sample is a biological sample; preferably plasma. In some embodiments, the biological particles are Lipoprotein (a) particles; and the fluorophore labeled entity is an aptamer or antibody capable of specifically binding Apolipoprotein (a). In some embodiments, the sample comprises one or more of the group consisting of high density lipoprotein (HDL), low density lipoprotein (LDL), intermediate density lipoprotein (IDL), very low density lipoprotein (VLDL), and oxidized LDL.

In some embodiments, the method further comprises contacting the sample with a second fluorophore labeled entity comprising fluorophore labeled aptamers or antigens capable of specifically binding Apolipoprotein A1 (Apo A1) and/or Apolipoprotein B (Apo B) prior to differential-charged particle mobility analysis, wherein the first and second fluorophore labeled entities have different fluorescence characteristics. In some related embodiments, the method further comprises contacting the sample with a third fluorophore labeled entity comprising a fluorophore labeled binding protein capable of specifically binding oxidized LDL prior to differential-charged particle mobility analysis, wherein the first, second, and third fluorophore labeled entities have different fluorescence characteristics.

In some embodiments, the biological particle is a protein. In some embodiments, the biological particle is a nucleic acid.

In some embodiments, the biological particle is a lipoprotein and the first fluorophore labeled entity is a lipophilic fluorophore. In related embodiments, the lipophilic fluorophore is selected from the group consisting of 1,1'-dioctadecyl-3,3,3',3'-tetramethylindocarbocynanine perchlorate (DiI), 3,3'-dioctadecyloxacarbocynanine perchlorate (DiO), 1,1'-dioctadecyl-3,3,3',3'-tetramethylindodicarbocynanine perchlorate (DiD), and 1,1'-dioctadecyl-3,3,3',3'-tetramethylindotricarbocynanine iodide (DiR), Alexa Fluor 488 (carboxylic acid, succinimidyl ester 'mixed isomers'), and fluorescein-5-EX, succinimidyl ester; preferably 1,1'-dioctadecyl-3,3,3',3'-tetramethylindocarbocynanine perchlorate (DiI) or Alexa Fluor 488 (carboxylic acid, succinimidyl ester 'mixed isomers').

In some embodiments, the first fluorophore labeled entity is a fluorophore labeled lipid. In some related embodiments, the fluorophore labeled lipid is labeled with a lipophilic fluorophore. In further related embodiments, the lipophilic fluorophore is selected from the group consisting of 1,1'-dioctadecyl-3,3,3',3'-tetramethylindocarbocynanine perchlorate (DiI), 3,3'-dioctadecyloxacarbocynanine perchlorate (DiO), 1,1'-dioctadecyl-3,3,3',3'-tetramethylindodicarbocynanine perchlorate (DiD), and 1,1'-dioctadecyl-3,3,3',3'-tetramethylindotricarbocynanine iodide (DiR), Alexa Fluor 488 (carboxylic acid, succinimidyl ester 'mixed isomers'), and fluorescein-5-EX, succinimidyl ester; preferably 1,1'-dioctadecyl-3,3,3',3'-tetramethylindocarbocynanine perchlorate (DiI) or Alexa Fluor 488 (carboxylic acid, succinimidyl ester 'mixed isomers').

DETAILED DESCRIPTION OF THE INVENTION

Figure 1:
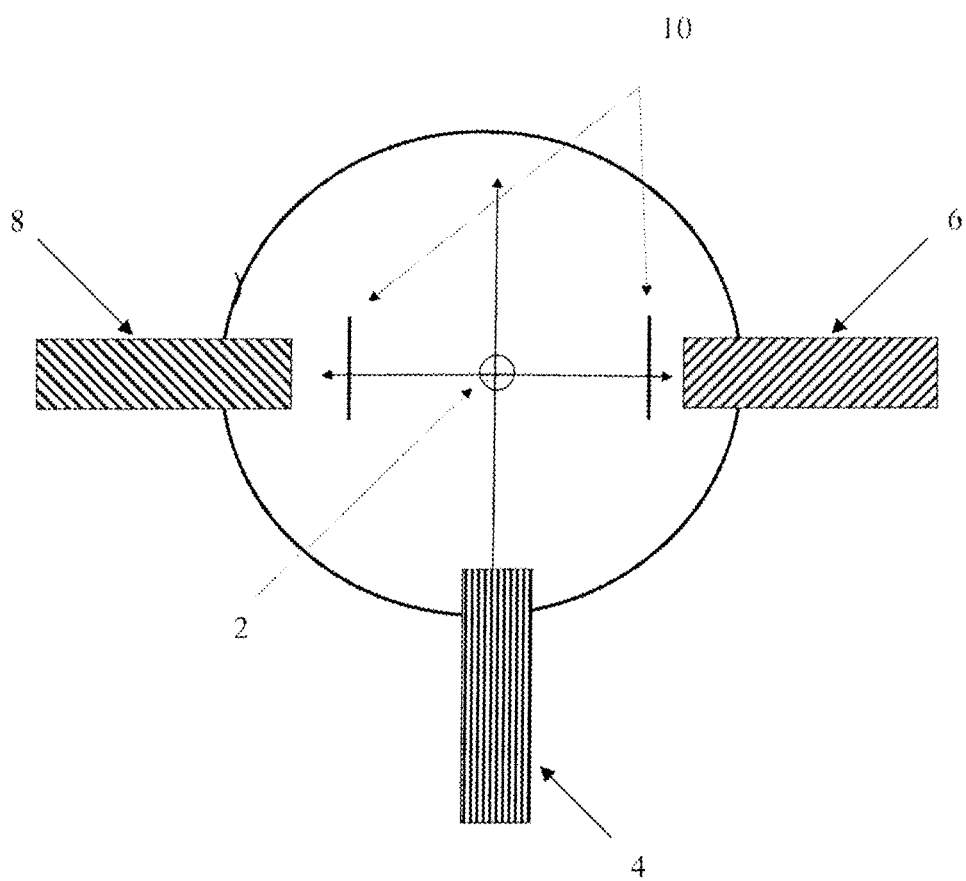
FIG. 1 shows a cross-sectional schematic of one possible arrangement of a fluorescence excitation source and multiple fluorescence detectors around the laminar-flow air stream.

The present invention contemplates ion mobility analysis systems for differential-charged particle mobility analysis and fluorescence detection, methods of preparation of samples for differential-charged particle mobility analysis and fluorescence detection, and methods of differential-charged particle mobility analysis and fluorescence detection.

Differential-charged particle mobility analysis utilizes the principle that particles of a given size and charge state behave in a predictable manner when carried in a laminar-air flow passed through an electric field. Accordingly, differential-charged particle mobility analysis is a technique to determine the size of a charged particle undergoing analysis when the charged particle is exposed to an electric field.

Electrical mobility is a physical property of an ion and is related to the velocity an ion acquires when it is subjected to an electrical field. Electrical mobility, Z, is defined as $$Z = \frac{V}{E} \quad (1)$$

where V=terminal velocity and E=electrical field causing particle motion. Particle diameter can be obtained from $$Z = \frac{neC_c}{3\pi\eta d} \quad (2)$$

where n=number of charges on the particle (in this case a single charge), e=1.6×10$^{-19}$ coulombs/charge, $C_c$=particle size dependent slip correction factor, η=gas viscosity, and d=particle diameter. Accordingly, solving for d provides the following relationship:

$$d = \frac{neC_c}{3\pi\eta} \frac{E}{V}. \quad (3)$$

Thus, an explicit relationship for particle diameter as a function of known parameters results. By setting the parameters to different values, different particle diameters of the charged particles may be selected as further described below and known in the art. In preferred methods of differential-charged particle mobility analysis, the electric field strength E acting upon the charged particle is varied during analysis.

In differential-charged particle mobility analysis, particles (e.g., lipoproteins and the like) are carried through the system using a series of laminar airflows. The particles in a volatile solution are introduced to an electrospray chamber containing approximately 5% $CO_2$ wherein the particles desolvate. In the electrospray chamber, the desolvated charged particles are subjected to ionized air, introduced for limitation by an alpha particle emitter in the chamber. Based on Fuch's formula, a predictable proportion of particles emerge from the chamber carrying a single charge and are transported from the chamber to the Differential Mobility Analyzer (DMA). For details on Fuch's formula, reference is made to Fuchs, N.A.: *The Mechanics of Aerosols*, Macmillan, 1964. Detailed descriptions of various components useful in one type of differential-charged particle mobility analyzer are found in Caulfield, et al. (U.S. patent application Ser. No. 11/760,672, filed Jun. 8, 2007, and Ser. No. 11/760,700, filed Jun. 8, 2007; incorporated by reference herein in their entirety).

As used herein, "Differential Mobility Analyzer," "DMA" and like terms refer to devices for classifying charged particles on the basis of ion electrical mobility, as known in the art and described herein.

In differential-charged particle mobility analysis, the size of particles with a known uniform charge may be determined from the mobility thereof. In the DMA, the particles enter at the top outer surface of the chamber and are carried in a fast flowing laminar-air flow (i.e., "the sheath flow"). The sheath flow is filtered air recirculated through the DMA at a constant velocity, for example without limitation of about 20 L/min. This velocity, however, can be varied to facilitate collection of particles of different sizes. As the particles pass through the DMA (carried in the sheath flow) the electric potential across the chamber is ramped up at a known rate. As the electrical potential changes, particles of different diameter are collected via a slit at the bottom inner surface of the chamber. Particles follow a non-linear path through the DMA depending on their charge and diameter. At any given electrical potential, particles of known size will follow a path that will allow them to pass through the collecting slit. Particles passing through the collecting slit are picked up by another, separate laminar-flow air stream and are carried to a detection system.

Ion mobility analysis systems of the present invention utilize differential-charged particle mobility analysis in conjunction with fluorescence detection. Thus, in the ion mobility analysis system of the present invention, the detection system comprises a condenser, a fluorescence detection system, and a particle detection and counting system.

Figure 4:
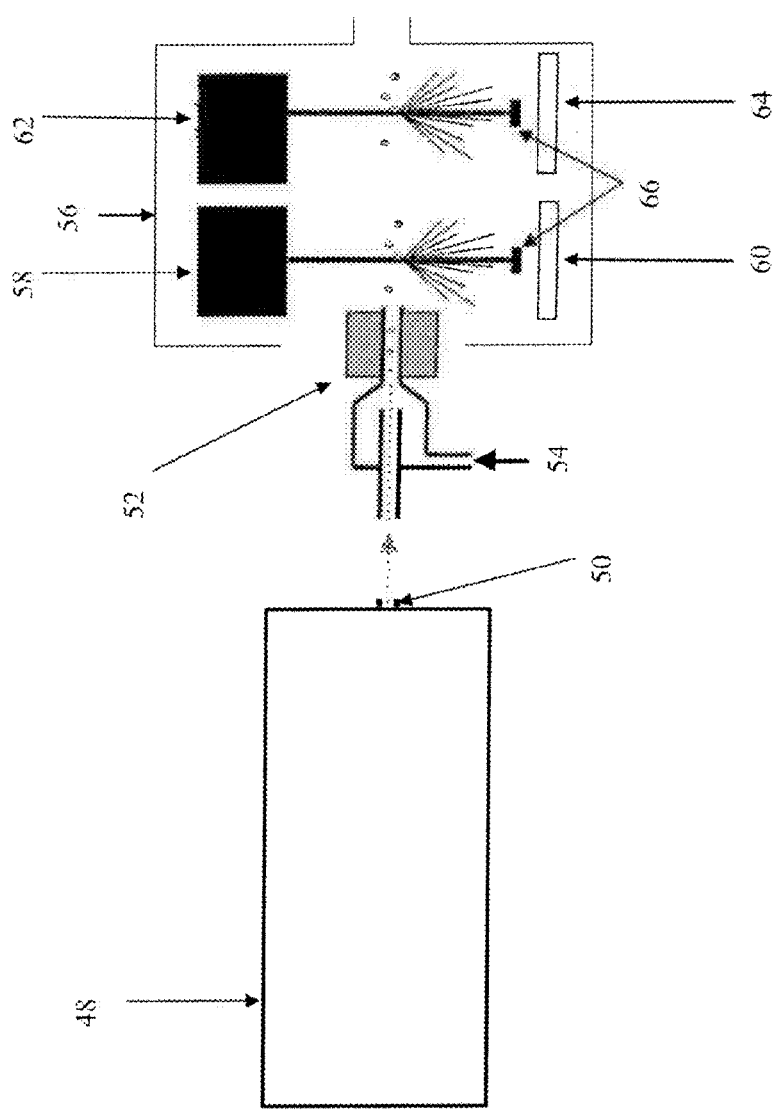
FIG. 4 shows a schematic of one possible apparatus for differential-charged particle mobility analysis and fluorescence detection with sequential particle detector/counter and fluorescence detection systems. In the example shown, the particle detector/counter system is upstream of the fluorescence detection system.
Figure 5:
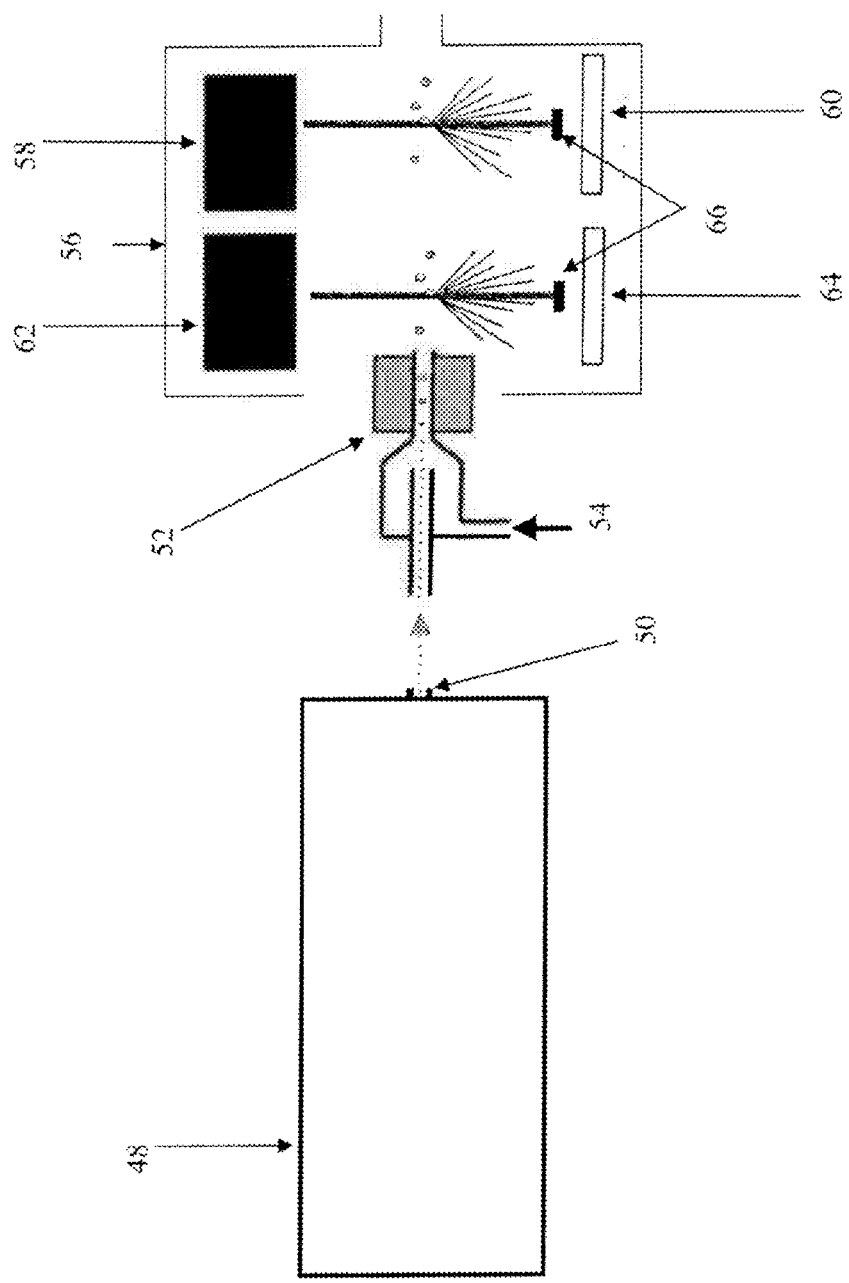
FIG. 5 shows a schematic of one possible apparatus for differential-charged particle mobility analysis and fluorescence detection with sequential particle detector/counter and fluorescence detection systems. In the example shown, the fluorescence detection system is upstream of the particle detector/counter system.
Figure 6:
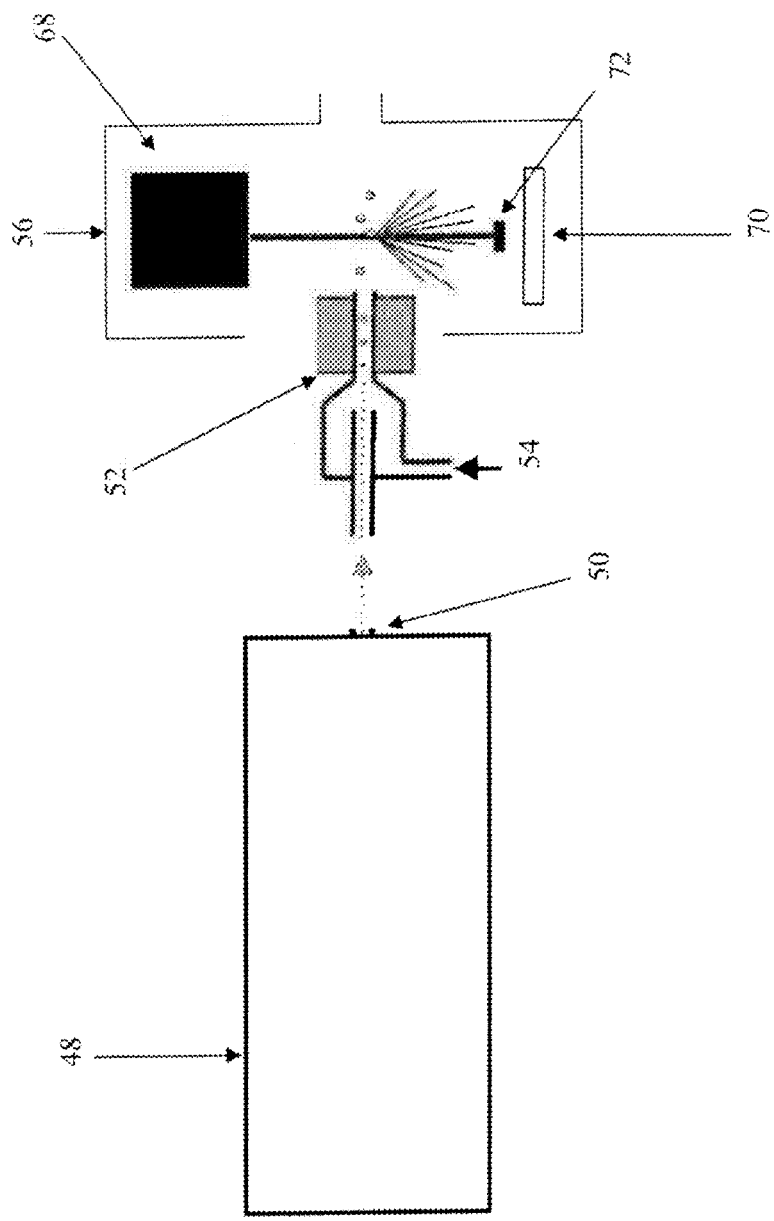
FIG. 6 shows a schematic of one possible apparatus for differential-charged particle mobility analysis and fluorescence detection with a single detection system for simultaneous particle detection/counting and fluorescence detection.

Schematic representations of exemplary ion mobility analysis systems of the present invention are shown in FIGS. 4-6. These figures illustrate three exemplary configurations of various detection system components. In the demonstrated systems, the sample undergoes differential-charged particle mobility analysis at 48 prior to reaching the detection system. Particles exit the differential-charged particle mobility analysis device 48 at port 50 carried in a laminar-flow air stream.

As the laminar-flow air stream carrying the particles enters the detection system, the particles pass through a condenser 52. The condenser enlarges the particles by condensation to a size that can be detected and counted, for example by a laser detection system. Multiple orientations of the remaining components are possible and description of the following examples are not meant to be limiting. As seen in FIG. 4, the particles emerge from the condenser into a light tight enclosure 56 containing a particle detection and counting system and a fluorescence detection system. FIG. 4 shows an example in which the particle detection and counting system is upstream of the fluorescence detection system. The particle detection and counting system contains an excitation source 58, such as a laser, and a detector 60. Such particle detection and counting systems are well known in the art. The fluorescence detection system comprises an excitation source 62, such as a laser, and a fluorescence detector 64.

The arrangement illustrated in FIG. 5 is distinguished from the arrangement described above in that the fluorescence detection system is located upstream relative to the particle detection and counting system; i.e., particles exiting the condenser 52 must first pass through the fluorescence detection system (excitation source 62 and fluorescence detector 64) before passing through the particle detection and counting system (excitation source 58 and detector 60).

The arrangement illustrated in FIG. 6 contains only a single excitation source 68 which is used in a combined particle detection and counting and fluorescence detection system. In this arrangement, particles exit condenser 52 and pass through the combination detection system. The combination detection system has a single excitation source 62 a detector array 70. The details are not shown in FIG. 6, however, detector array 70 contains a particle detection and counting system (e.g. a scattering detector) and at least one fluorescence detector. More complicated arrays are possible and are described below.

In some embodiments, excitation source(s) and fluorescence detector(s) are positioned on either side of the charged particle flow such that the particle flow passes between excitation source/fluorescence detector pairs. Configured in this way, fluorescence detection systems utilizing multiple pairs of excitation sources/fluorescence detectors are arranged such that the particle flow passes between pairs sequentially. In other embodiments, multiple excitation sources and/or detectors may be arranged in an array located around the flow path. In related embodiments, the excitation sources and/or detectors in this array may be arranged annularly. Any resulting fluorescence is detected, e.g. through the selective orientation and use of light filters and detectors well known in the art.

The particles that exit the condenser are also detected and counted with a particle detection and counting system, such as a laser detection system. The detection and counting system may be combined with the fluorescence detection system such that detection and counting of charged particles occurs concurrently with fluorescence detection. Alternatively, the detection and counting system may be located upstream or downstream of the fluorescence detection system such that fluorescence detection and particle detection and counting occur sequentially. Knowing the electrical potential being applied to the DMA when the particle was collected permits accurate determination of the particle diameter and the number of particles present at that size.

Data generated by the fluorescence detection and particle detection and counting systems is collected and stored in bins, for example on a computer as a user-accessible database, as a function of time for different particle sizes. In this way the number of particles of any given size range can be determined and converted to a concentration of particles based on the time required to collect the data, the flow rate of sample being introduced into the electrospray device, and the number of charged particles of the size range.

In embodiments of the first aspect of the invention, the fluorescence detector system comprises at least one excitation source such as a laser and at least one suitable fluorescence detector, for example between one and seven fluorescence detectors.

Possible types of excitation sources that could be used in this application include fixed wavelength lasers or continuous-wavelength lasers (sometimes referred to as tunable lasers). The fixed wavelength laser may emit at a single wavelength (such as a Nitrogen laser) or multiple wavelengths simultaneously (such as a Argon laser or a He—Ne laser).

Continuous-wavelength lasers can provide various excitation wavelengths in a controlled manner.

The excitation source may be operated either in a continuous wave mode, in which the output of the laser is relatively consistent with time, or in a pulsed mode, in which the laser is fired when a particle is detected. The relative orientation of an excitation source and fluorescence detector(s) may be different depending on which of these operational methods is utilized. For example, if an excitation source is operating in a pulsed mode, the excitation source and fluorescence detector(s) will be located downstream relative to the particle detection and counting system (FIG. 4). In this orientation, the particle detection and counting system may be used as a trigger to initiate the pulsed fluorescence excitation source. However if the excitation source is operating in a continuous mode, the excitation source and fluorescence detectors may be located upstream relative to (FIG. 5), in the same array as (FIG. 6), or downstream relative to (FIG. 4) the particle detection and counting system. Of the possible orientations for a continuous excitation source, arranging the excitation source and fluorescence detector(s) to be located in the same array as the particle detection and counting system (FIG. 6) is preferred, so that particles can be detected/counted and fluoresced at the same time.

Any suitable fluorescence detector known in the art may be used. An example of a suitable fluorescence detector is a wavelength specific photomultiplier tube. If multiple fluorescence detectors are utilized in the fluorescence detector system, the detectors may be arranged in an array with a single excitation source.

One exemplary arrangement of a detector system utilizing a single excitation source and two detectors is illustrated in FIG. 1, which presents the particle stream 2 in cross-section. In this example, the fluorescence detection system comprises a single excitation source 4 at wavelength $\lambda_1$, and two fluorescence detectors 6 and 8 that detect at different wavelengths $\lambda_2$ and $\lambda_3$. The arrangement illustrated in FIG. 1 includes an excitation source 4 and detectors 6 and 8 arranged such that the angle between the excitation source 4 and either detector 6 or 8 is approximately 90° and the angle between the two detectors 6 and 8 is approximately 180°. This configuration is not meant to be limiting as fewer or additional detectors may be present and numerous orientations are possible for any excitation source/detector array. As is well known in the art, an appropriate filter or $\lambda$ specific mirror 10 may be used in combination with any detector so that only a specific $\lambda$ or $\lambda$ range is detected by the detector.

Figure 2:
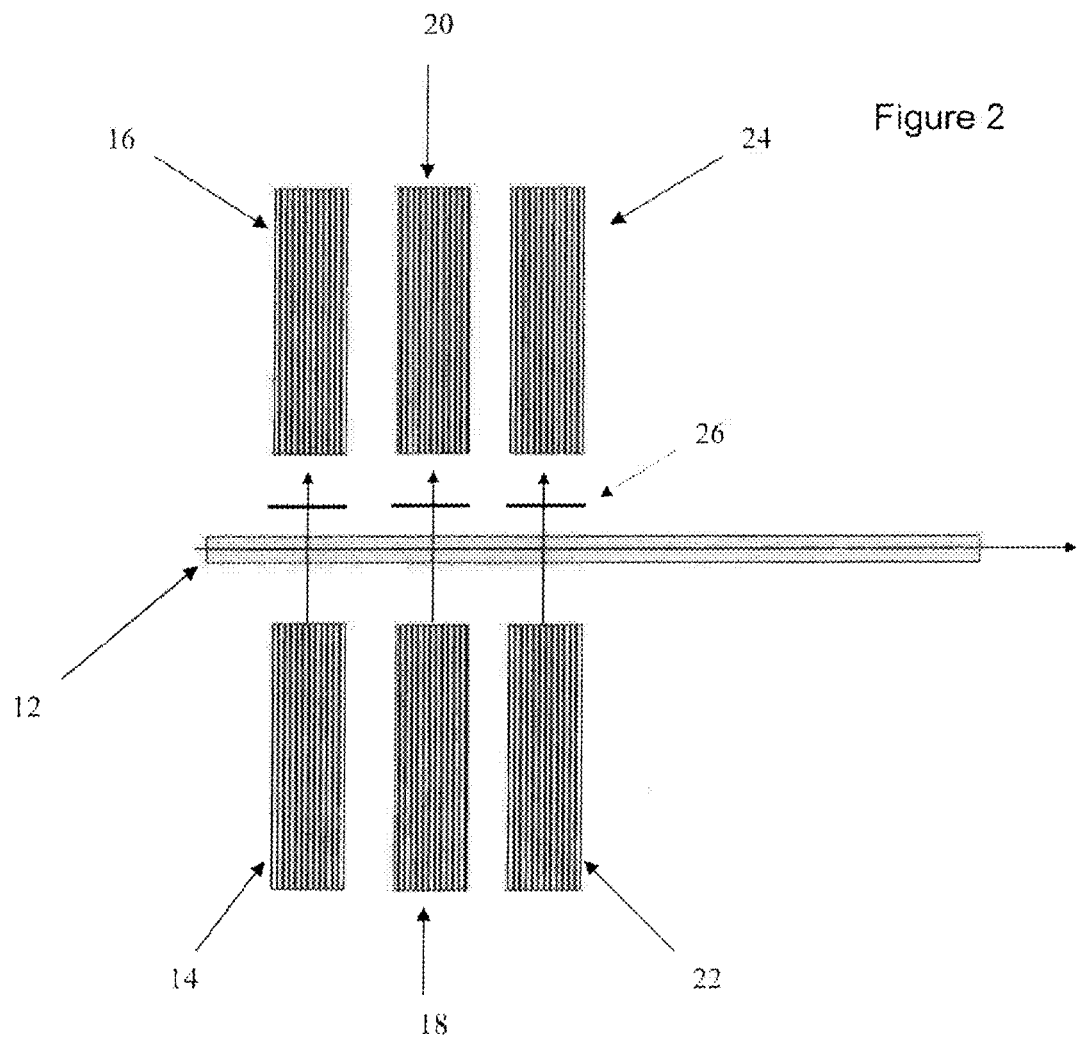
FIG. 2 shows an in-perspective schematic of a second possible arrangement of multiple fluorescence excitation sources and multiple fluorescence detectors arranged linearly along the laminar-flow air stream.

Alternatively, each detector may have its own excitation source, with excitation source/detector pairs arranged sequentially along the laminar-flow air stream after the stream exits the condenser. In this arrangement, one or more excitation source/detector pairs may be used. An exemplary arrangement of three excitation source/detector pairs arranged in such a way is shown in FIG. 2, which presents the particle stream 12 in perspective. The example illustrated in FIG. 2 has three excitation sources 14, 18, and 22 at $\lambda_1$, $\lambda_3$, and $\lambda_5$. The $\lambda$ of any excitation source may be the same as or may be different from the $\lambda$ of any other excitation source. Each excitation source has its own fluorescence detector 16, 20, and 24. A different filter or $\lambda$ specific mirror 26 may be used for each fluorescence detector so that each excitation source/fluorescence detector pair can be used to detect fluorescence at a different $\lambda$ or $\lambda$ range. The example illustrated in FIG. 2 has each detector facing the particle beam directly opposite its excitation source. This arrangement is not meant to be limiting, as numerous orientations are possible; i.e., the angle between an excitation source and its fluorescence detector may be some angle other than about 180°, such as about 90°.

Figure 3:
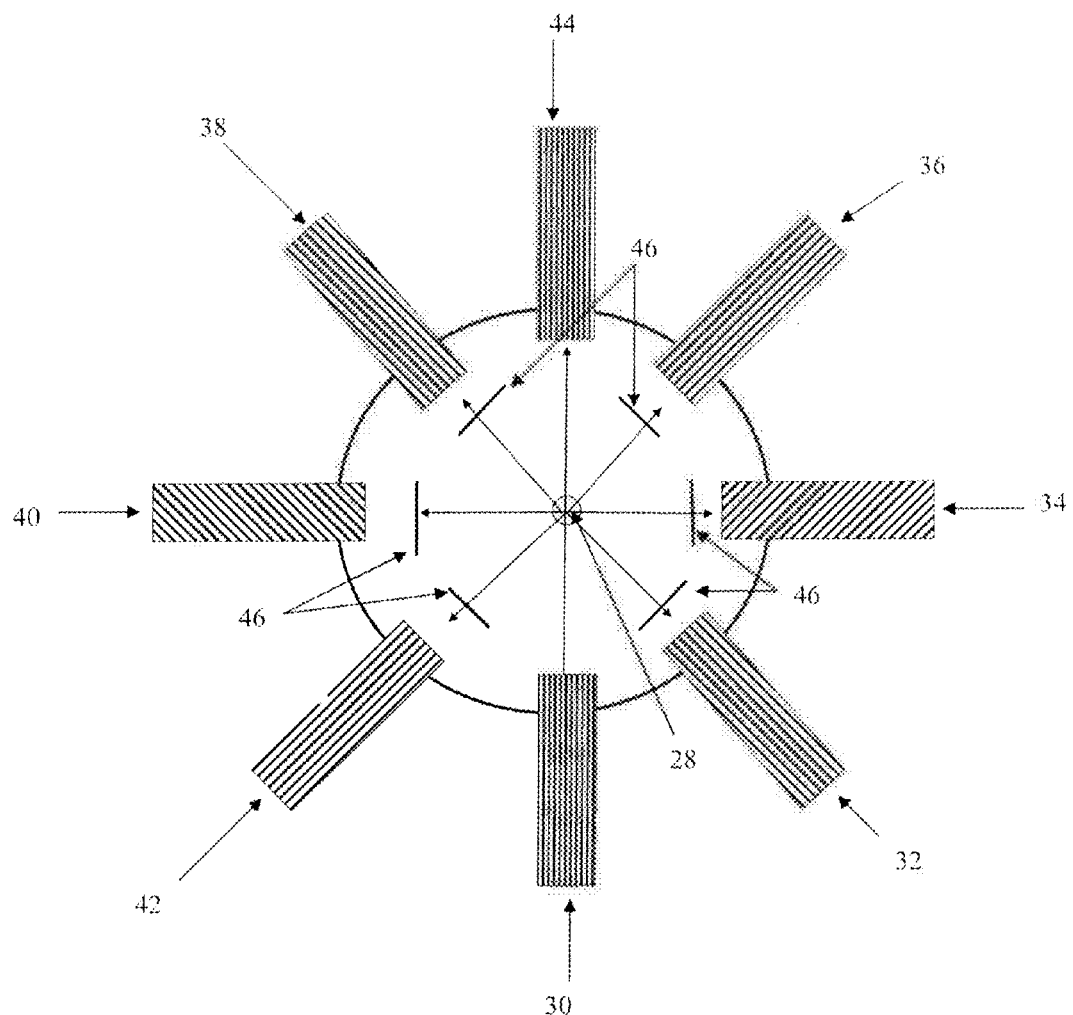
FIG. 3 shows a cross-sectional schematic of a third possible arrangement of a single fluorescence excitation source and multiple fluorescence detectors arranged in an annular fashion surrounding the path of the laminar-flow air stream.

In some embodiments, the fluorescence detection system comprises an excitation source and multiple detectors arranged in an annular array surrounding the path of the laminar-flow air stream after the stream exits the condenser. In these embodiments, a particle detection and counting system, such as a laser detection (or light scattering) system, may also be incorporated into the annular array. A schematic of one such possible arrangement is illustrated in FIG. 3, which presents the particle stream 28 in cross section. The example illustrated in FIG. 3 utilizes a single excitation source 30 at $\lambda_1$ that serves the dual purpose of being the fluorescence excitation source as well as the laser source in the particle detection and counting system. A light scatter detector 44 is positioned in the array opposite the excitation source 30 for use as the detector in the particle detection and counting system. In alternative arrangements, the particle detection and counting system may be located upstream or downstream of the excitation source(s) and fluorescence detector(s). As discussed above, the relative orientation of the fluorescence detection system and the particle detection and counting system may be limited based on the operational mode of the excitation source employed. One or more fluorescence detectors are positioned at other locations in the array. In the example in FIG. 3, fluorescence detectors 32, 34, 36, 38, 40, and 42 are positioned such that the angle between any two adjacent components is about 45°. However, this specific example is not meant to be limiting, as fewer or additional fluorescence detectors may be included in the array. As in the above described examples, a different filter or $\lambda$ specific mirror 46 may be used for each fluorescence detector so that each fluorescence detector can be used to detect fluorescence at a different $\lambda$ or $\lambda$ range.

To obtain more accurate biological particle profiles using differential-charged particle mobility analysis discussed above, it is desirable to adjust results of analysis for any loss of biological particles during handling (e.g. sample centrifugation, pipetting and dilutions) prior to introduction of the sample into the differential-charged particle mobility analysis apparatus. In a second aspect of the invention, fluorophore labeled particles are added to a sample at a known concentration for use as an internal standard. By following the label during processing, the recovery of the labeled particles can be used to adjust the detected concentrations of similar but unlabeled particles also present in the sample. Quantitation of recovery is accomplished by confirming the identity of particles of a given size range by the detection of fluorescence in the fluorescence detector and determining the relationship between the derived concentrations of the fluorescence identified particles with their known starting concentration. In preferred embodiments, fluorophore labeled particles have sizes similar to unlabeled particles of interest in a sample. In more preferred embodiments, the labeled particles are analogs of the unlabeled particles of interest with an attached fluorophore. In alternative embodiments, the labeled particles have significantly different sizes than their unlabeled analogues. In either instance, the recovery rate of fluorophore labeled particles is assumed to be the same as their unlabeled analogues.

As used herein, "biological particle" refers to a molecule or non-covalently bound assembly of molecules derived from a living source of a size appropriate for analysis with an ion mobility analysis apparatus. Examples without limitation of biological particles are apolipoproteins, certain nucleic acids, certain proteins, lipoproteins assembled for example from apolipoproteins and lipids; viral components assembled from non-covalently bound coat proteins and glycoproteins; immune complexes assembled from antibodies and their cognate antigens, and the like. Appropriate sizes for analysis are preferably about 2 nm to about 400 nm.

In embodiments of the invention which contemplate biological particles, the biological particles may derive from a biological specimen, obtained by methods well known in the art or as described herein. The terms "biological specimen," "biological sample" and like terms refer to explanted, withdrawn or otherwise collected biological tissue or fluid including, for example without limitation whole blood, serum, plasma, and other biological tissues and fluids. The term "plasma" in the context of blood refers to the fluid obtained upon separating whole blood into solid and liquid components. The term "serum" in the context of blood refers to the fluid obtained upon separating whole blood into solid and liquid components after it has been allowed to clot. In some embodiments, the biological specimen is of human origin. In some embodiments, the biological specimen is serum. In some embodiments, the biological specimen is plasma.

The terms "lipoprotein" and "lipoprotein particle" as used herein refer to particles obtained from mammalian blood which include apolipoproteins biologically assembled with noncovalent bonds to package for example, without limitation, cholesterol and other lipids. Lipoproteins preferably refer to biological particles having a size range of about 7 nm to about 120 nm, and include VLDL (very low density lipoproteins), IDL (intermediate density lipoproteins), LDL (low density lipoproteins), Lp(a) (lipoprotein (a)), HDL (high density lipoproteins) and chylomicrons as defined herein.

As used herein, "VLDL", "IDL", "LDL", and "HDL" refer to classifications of lipoproteins as shown in Table 1. It is understood that the values used in Table 1 for particle diameter are determined by gel electrophoresis methods, as known in the art. With the ion mobility analysis methods described in Caulfield et al., it has been observed that lipoprotein diameters obtained with ion mobility analysis are smaller relative to diameters obtained with gel electrophoresis. Without wishing to be bound by any theory, it is believed that this difference is due to calibration of the gels. The shift appears to be linearly related and approximated by the following formula:

$$0.86 * \text{gel diameter} = IM \text{ diameter}$$

Table 1 describes the standard class and subclass designations assigned to various lipoprotein fractions using traditional gel electrophoresis measurements: very low density lipoproteins (VLDLs) with subclasses VLDL I and II; intermediate density lipoproteins (IDLs) with subclasses IDL I and II; low density lipoproteins (LDLs) with subclasses I, IIa, IIb, IIIa, IIIb, IVa and IVb; and high density lipoproteins (HDLs), which typically includes several subclasses, such as HDL IIa, IIb, IIa, IIIb, and IIIc.

TABLE 1

Major Lipoprotein Class, Subclass, Density and Particle Size

| Class Acronym Subclass | Name Density (g/mL) | Particle Diameter (Å) |
|---|---|---|
| VLDL | Very Low Density Lipoprotein | |
| I | <1.006 | 330-370 |
| II | 1.006-1.010 | 300-330 |
| IDL | Intermediate Density Lipoprotein | |
| I | 1.006-1.022 | 285-300 |
| II | 1.013-1.019 | 272-285 |
| LDL | Logy Density Lipoprotein | |
| I | 1.019-1.023 | 272-285 |

TABLE 1-continued

Major Lipoprotein Class, Subclass, Density and Particle Size

| Class Acronym Subclass | Name Density (g/mL) | Particle Diameter (Å) |
|---|---|---|
| IIa | 1.023-1.028 | 265-272 |
| IIb | 1.028-1.034 | 256-265 |
| IIIa | 1.034-1.041 | 247-256 |
| IIIb | 1.041-1.044 | 242-247 |
| IVa | 1.044-1.051 | 233-242 |
| IVb | 1.051-1.063 | 220-233 |
| HDL | High Density Lipoprotein | |
| IIa | 1.063-1.100 | 98-130 |
| IIb | 1.100-1.125 | 88-98 |
| IIIa | 1.125-1.147 | 82-88 |
| IIIb | 1.147-1.154 | 77-82 |
| IIIc | 1.154-1.203 | 72-77 |

Without wishing to be bound by theory, it is believed that the observed differences between ion mobility analysis diameters and gel electrophoresis diameters may also be due to distortion of lipoproteins interacting with the gel matrix under the influence of the intrinsic impressed electric field of the electrophoresis gel. The size difference may also be due to historical data used to convert particle density (obtained from analytic ultracentrifuge separations) to particle size obtained from electron microscopy.

The term "apolipoprotein" as used herein refers to lipid-binding proteins which constitute lipoproteins. Apolipoproteins are classified in five major classes: Apo A, Apo B, Apo C, Apo D, and Apo E, as known in the art.

As used herein, "Apo A1" or "apolipoprotein A1" is the protein known in the art as a protein component of HDL. As used herein, "Apo(a)" or "apolipoprotein a" is the protein known in the art as a protein component of Lp(a). As used herein, "Apo B" or "apolipoprotein B" is the protein known in the art as a protein component of LDL, IDL, and VLDL, and indeed is the primary apolipoprotein of lower density lipoproteins, having human genetic locus 2p24-p23. ApoB is also the primary apolipoprotein component of chylomicrons in the form of ApoB48.

In certain embodiments of the invention, the sample may be a complex sample or a purified sample. In some preferred embodiments, the sample is a purified lipoprotein sample. Purified samples of lipoproteins may be prepared by any method known in the art, including but not limited to centrifugation and non-centrifugation methods described in Caulfield, et al. In certain embodiments, the Lp(a) has been removed from the purified lipoprotein sample and the purified lipoprotein sample contains at least one from the group consisting of HDL, LDL, IDL, and VLDL.

As used herein, a "complex sample" is a sample that contains two or more of the following types of particles IDL, VLDL, LDL, HDL, Lp(a), nucleic acids, albumin, or other proteins.

As used herein, "albumin" refers to ubiquitous proteins constituting approximately 60% of plasma proteins, having density about 1.35 g/mL, as known in the art.

As used herein, "Lp(a)" and "lipoprotein (a)" refer to a type of lipoprotein found in serum having a molecular composition distinct from LDL and IDL. Lp(a) has a particle size that overlaps with LDL and IDL and therefore can erroneously contribute to quantitation of LDL and IDL based on particle size analysis when Lp(a) particles are present in the sample. Although some patients have naturally occurring low Lp(a) concentrations, it is believed to be good practice to remove the Lp(a) prior to LDL size measurements to preclude otherwise inaccurate measurements for those patients having significant Lp(a) concentrations. However, removal of Lp(a) particles is not necessary if Lp(a) particles are specifically labeled with a first fluorophore containing antibody or aptamer to Apo(a) and thus can be concurrently measured in a complex sample.

In a third aspect of the invention, detection and/or quantification of biological particles in a sample is accomplished with a differential-charged particle mobility analysis apparatus through the use of fluorescently labeled entities. Use of fluorescent labels in this aspect of the invention allows for detection and/or quantitation of a biological particle of interest without calibration of the instrument or purification of the sample, as appropriate fluorescently labeled entities are integrated into the particles of interest and measurements with a differential-charged particle mobility analysis apparatus are absolute. In preferred embodiments, labeling the biological particles of interest does not significantly affect their size. Alternatively, integrating the fluorescently labeled entity into the particle of interest may significantly affect the particle size. In these embodiments, it is desirable to know the size of the unlabeled particle and the magnitude of change caused by integrating the fluorescently labeled entity; however this information is not necessary for identifying the presence of the particle of interest as detection of fluorescently labeled particles is indicative of the presence of the biological particle of interest in the sample tested. In certain embodiments of this aspect, the sample is a biological sample, for example plasma.

As used herein, the term "integrating the fluorescently labeled entity into the particle of interest" is used to indicate that a fluorescently labeled entity has become attached to a particle of interest with sufficient stability so that the fluorescently labeled entity remains attached to the particle of interest while undergoing differential particle mobility analysis. Forces that give rise to and maintain this attachment are not intended to be limited in any way. For example, means of attachment may include ionic, electrostatic, Hydrogen-bond, van der Waals, or hydrophobic interactions.

In certain embodiments of this aspect, biological particles of interest may include but are not limited to nucleic acids, lipoproteins, or other proteins. Means for labeling particles with a fluorophore vary depending on the nature of the particles of interest and are well known in the art. Generally speaking, particles can be labeled with a fluorophore either externally or internally. Externally labeling a particle is accomplished by contacting the particle with a fluorescently labeled entity that integrates into the particle but does not replace some component of the particle. For example, LDL may be externally labeled with a lipophilic fluorophore or with a fluorophore labeled antibody or aptamer to Apo B; Lp(a) may be externally labeled with a fluorophore labeled antibody or aptamer to Apo(a); DNA may be externally labeled with a fluorophore labeled probe; and proteins may be externally labeled with an appropriate fluorophore labeled antibody or aptamer. Conversely, internally labeling a particle is accomplished by contacting the particle with a fluorescently labeled entity that integrates into the particle by replacing some component of the particle.

In certain preferred embodiments of this aspect, the biological particles of interest are Lp(a) particles and the fluorophore labeled entity is an aptamer or antibody capable of specifically binding Apo(a). In these embodiments, Lp(a) is fluorescently labeled with a first fluorophore containing an aptamer or antibody to Apo(a) so that Lp(a) can be identified and quantitated in a complex sample. This information can then be used to correct for the contribution of Lp(a) to the quantitation of LDL and IDL sized particles.

In related embodiments, Lp(a) is fluorescently labeled with a first fluorophore containing aptamer or antibody to Apo(a) and HDL, LDL, IDL and VLDL are labeled with second fluorophore containing aptamers or antibodies to Apo A1 and Apo B. In these embodiments, the first and second fluorophores have different fluorescence characteristics, i.e., different excitation and/or emission wavelengths.

In other related embodiments, Lp(a) is fluorescently labeled with a first fluorophore containing aptamer or antibody to Apo(a); HDL, LDL, IDL and VLDL are labeled with second fluorophore containing aptamers or antibodies to Apo A1 and Apo B; and oxidized LDL is labeled with a third fluorophore containing binding-protein. In these embodiments, the first, second and third fluorophores each have different fluorescence characteristics, i.e., different excitation and/or emission wavelengths.

In other embodiments of this aspect, the biological particle of interest is a nucleic acid. In these embodiments, a fluorophore labeled entity able to specifically bind to the nucleic acid of interest is used. Preparation of probes (both labeled and unlabeled) capable of specifically binding a particular nucleic acid is well known in the art.

In other embodiments of this aspect, the biological particle of interest is a protein other than a lipoprotein. In these embodiments, a fluorophore labeled entity able to specifically bind to the protein of interest is used. Preparation of entities (both labeled and unlabeled) capable of specifically binding a particular protein is well known in the art.

In certain embodiments of this aspect, the biological particles of interest are lipoprotein particles and the fluorophore labeled entity is a lipophilic fluorophore. In these embodiments, lipoproteins are externally labeled with the lipophilic fluorophore by contacting the lipoproteins with the lipophilic fluorophore.

The term "lipophilic fluorophore" refers to highly fluorescent lipophilic dyes that diffuse into the hydrophobic portion of the LDL complex without affecting LDL-specific binding of the apoprotein. Examples of suitable dyes include, but are not limited to lipophilic carboncyanines such as 1,1'-dioctadecyl-3,3,3',3'-tetramethylindocarbocynanine perchlorate (DiI), 3,3'-dioctadecyloxacarbocynanine perchlorate (DiO), 1,1'-dioctadecyl-3,3,3',3'-tetramethyl indodicarbocynanine perchlorate (DiD), and 1,1'-dioctadecyl-3,3,3',3'-tetramethylindotricarbocynanine iodide (DiR). Such dyes are typically weakly fluorescent in water but highly fluorescent and photostable once incorporated into lipids. Other lipophilic dyes may be useful in the present invention including some well known in the art such as AlexaFluor 488 (carboxylic acid, succinimidyl ester 'mixed isomers', Molecular Probes Cat # A-20000, Mol. Wt. 643.42, Abs @494 nm/Em 517 nm) and fluorescein-5-EX, succinimidyl ester (Molecular Probes Cat # F-6130, Mol. Wt. 590.56, Abs @491 nm/Em 515 nm).

In certain related embodiments, the lipophilic fluorophore is selected from the group of fluorescent lipophilic dyes consisting of but not limited to lipophilic carboncyanines such as 1,1'-dioctadecyl-3,3,3',3'-tetramethylindocarbocynanine perchlorate (DiI), 3,3'-dioctadecyloxacarbocynanine perchlorate (DiO), 1,1'-dioctadecyl-3,3,3',3'-tetramethylindodicarbocynanine perchlorate (DiD), and 1,1'-dioctadecyl-3,3, 3',3'-tetramethylindotricarbocynanine iodide (DiR). In other related embodiments, the lipophilic fluorophore is 1,1'-dioctadecyl-3,3,3',3'-tetramethylindocarbocynanine perchlorate (DiI); or other dyes such as such as Alexa Fluor 488 (carboxylic acid, succinimidyl ester 'mixed isomers', Molecular Probes Cat # A-20000, Mol. Wt. 643.42, Abs @494 nm/Em 517 nm) and fluorescein-5-EX, succinimidyl ester (Molecular Probes Cat # F-6130, Mol. Wt. 590.56, Abs @491 nm/Em 515 nm).

In other embodiments, the biological particles of interest are lipoprotein particles and the fluorophore labeled entity is a fluorescently labeled lipid. In these embodiments, lipoprotein particles are labeled with the fluorescently labeled lipid by contacting the particles with the fluorescently labeled lipid. After contacting the lipoprotein particles with the labeled lipid, the sample may be incubated for a period of time to allow the labeled lipid to integrate into the lipoprotein particles by replacing a lipid component of the lipoprotein particles. Fluorescently labeled lipids useful in these embodiments may be made by any method known in the art. In certain related embodiments, the fluorescently labeled lipids are labeled with a lipophilic fluorophore, such as those described above.

In some embodiments, fluorescent entities may utilize the principle of fluorescence quenching and involve a donor fluorophore and a quenching moiety.

The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency than it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET").

In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a longer wavelength. Proximal quenching requires very close positioning of the donor and quencher moiety, while FRET quenching, also distance related, occurs over a greater distance (generally 1-10 nm, the energy transfer depending on R-6, where R is the distance between the donor and the acceptor). Thus, when FRET quenching is involved, the quenching moiety is an acceptor fluorophore that has an excitation frequency spectrum that overlaps with the donor emission frequency spectrum. When quenching by FRET is employed, the assay may detect an increase in donor fluorophore fluorescence resulting from increased distance between the donor and the quencher (acceptor fluorophore) or a decrease in acceptor fluorophore emission resulting from decreased distance between the donor and the quencher (acceptor fluorophore).

The term "aptamer" refers to macromolecules composed of nucleic acid, such as RNA or DNA, that bind tightly to a specific molecular target. The terms "bind," "binding" and the like refer to an interaction or complexation resulting in a complex sufficiently stable so as to permit separation. In some embodiments, the aptamer specifically binds Apo A1, Apo B, or Apo(a). Methods for the production and screening of aptamers useful for the present invention are well known in the art; see e.g., Griffin et al., U.S. Pat. No. 5,756,291, incorporated herein by reference in its entirety and for all purposes.

As practiced in the art, the method of selection (i.e., training) of an aptamer requires a pool of single stranded random DNA oligomers comprising both random sequences and flanking regions of known sequence to serve as primer binding sites for subsequent polymerase chain reaction (PCR) amplification. Such DNA oligomers are generated using conventional synthetic methods well known in the art. As an initial and optional step, PCR amplification is conducted by conventional methods, and the amplified pool is left as duplex DNA, or used as single stranded DNA after strand separation. Optionally, transcription into RNA can be conducted. The term "oligomer pool" in this context refers to such single stranded or duplex DNA, or RNA transcribed therefrom. The term "refined oligomer pool" refers to an oligomer pool which has been subjected to at least one round of selection as described herein.

Further the aforementioned aptamer training, a "selection" step is conducted employing a column or other support matrix (i.e., target-coupled support) having target molecule attached thereon. Attachment, well known in the art, may be by covalent or non-covalent means. The oligomer pool, or refined oligomer pool, and target-coupled support are incubated in order to permit formation of oligonucleotide-target complex, and the uncomplexed fraction of the oligomer pool or refined oligomer pool is removed from the support environment by, for example, washing by methods well known in the art. Subsequent removal of oligonucleotide by methods well known in the art results in a refined oligomer pool fraction having enhanced specificity for a target relative to a predecessor oligomer pool or refined oligomer pool.

In a typical production training scheme, oligonucleotide recovered after complexation with target or other constituent of the biological sample is subjected to PCR amplification. The selection/amplification steps are then repeated, typically three to six times, in order to provide refined oligomer pools with enhanced binding and specificity to target or other constituent of the biological sample. Amplified sequences so obtained can be cloned and sequenced. Optionally, when a plurality of individual aptamer sequence specific for a target having been obtained and sequenced, pairwise and multiple alignment examination, well known in the art, can result in the elucidation of "consensus sequences" wherein a nucleotide sequence or region of optionally contiguous nucleotides are identified, the presence of which correlates with aptamer binding to target. When a consensus sequence is identified, oligonucleotides that contain the consensus sequence may be made by conventional synthetic or recombinant means.

The term "antibody" refers to an immunoglobulin which binds antigen (e.g., lipoprotein or other component of the sample) with high affinity and high specificity. In this context "high affinity" refers to a dissociation constant of, for example without limitation 1 µM, 100 nM, 10 nM, 1 nM, 100 pM, or even more affine, characterizing the binding reaction of antibody with antigen to which the antibody has been raised. The term "raised" refers to the production of high affinity antibody by methods long known in the art. Further in this context, the term "high specificity" refers to a preference of binding of a target antigen by a test antibody relative to non-target antigen characterized by a ratio of dissociation constants of for example without limitation 1, 2, 5, 10, 20, 50, 100, 200, 500, 1000, 10000, or more, in favor of binding of the target antigen to which the test antibody has been raised.

Antibodies and aptamers contemplated for use in the present invention include, for example without limitation, fluorophore containing derivatives of antibodies and aptamers capable of specifically binding particles of interest.

The terms "about" and "similar" as used herein as related to a numerical value represents the value +/−10% thereof. Conversely, the use of the term "significantly different" to describe the relationship of two numbers indicates that the two numbers are not within +/−10% of each other.

EXAMPLES

Example 1

HDL Subfraction Labeling with Fluorescent Probes

The following method was used to conjugate a fluorescent molecule to HDL subfractions. This method may be applied to other types of lipoproteins. HDL was isolated from plasma by sequential flotation to obtain lipoproteins within density interval 1.063-1.20 g/mL. The total HDL fraction was then dialyzed to salt background density 1.184 g/mL and centrifuged for 28 hrs at 40,000 rpm, 10° C. in a fixed angle 50.3 Beckman rotor. The 6 ml centrifuge tube was then pipetted to obtain predominantly large, intermediate and small HDL subfractions, T[0-1], T[1-3] and T[3-6], respectively. The subfractions were then dialyzed against 100 mM NaHCO$_3$, pH 8.5, 4° C. overnight. Protein concentration was measured in each subfraction using the Lowry method.

HDL subfractions were then labeled with fluorescent probe Alexa Fluor 488 (carboxylic acid, succinimidyl ester 'mixed isomers', Molecular Probes Cat #A-20000, Mol. Wt. 643.42, Abs @494 nm/Em 517 nm; i.e., "AF488") according to manufacturer's instructions. Briefly, HDL subfractions were combined with AF488 at a suggested optimal ratio 10:1 (wt:wt) maintaining optimal concentrations of HDL and AF488, >2 mg/ml and 10 mg/ml, respectively. The protocol and quantities of the solutions used are listed in Table 2 below.

Example 2

Differential-Charged Particle Mobility Analysis of Alexa Fluor 488 Labeled LDL

Invrogen product L23380 contains 1 mg/mL of human LDL particles labeled with AF488, a highly fluorescent dye. Alexa Fluor 488 labeled LDL particles were subjected to differential-charged particle mobility analysis to assess the effect of fluorescence labeling on the size of the particles relative to unlabeled particles.

Figure 7:
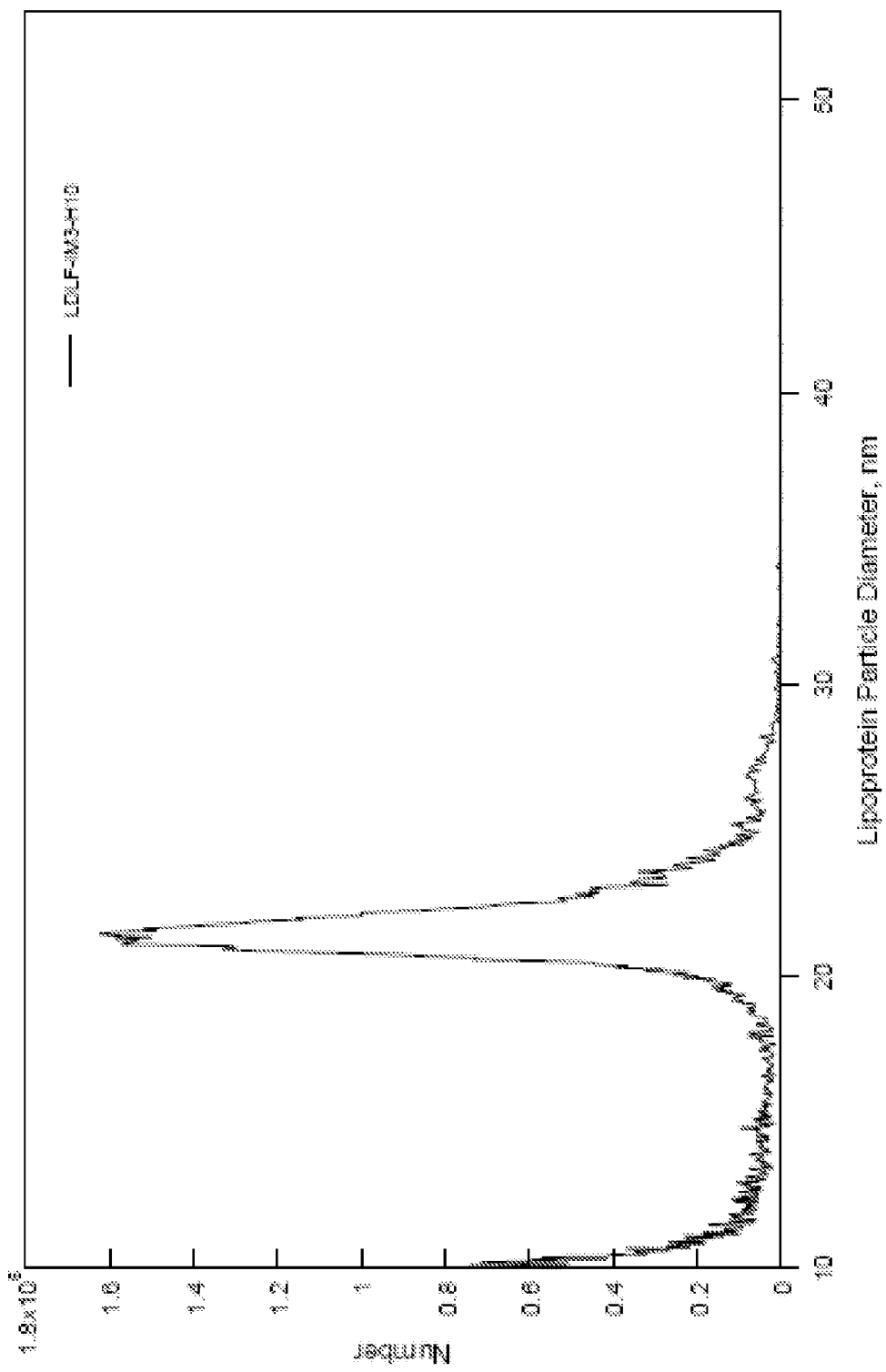
FIG. 7 demonstrates a particle number versus size profile generated from a sample of the Alexa Fluor 488 labeled particles.
Figure 8:
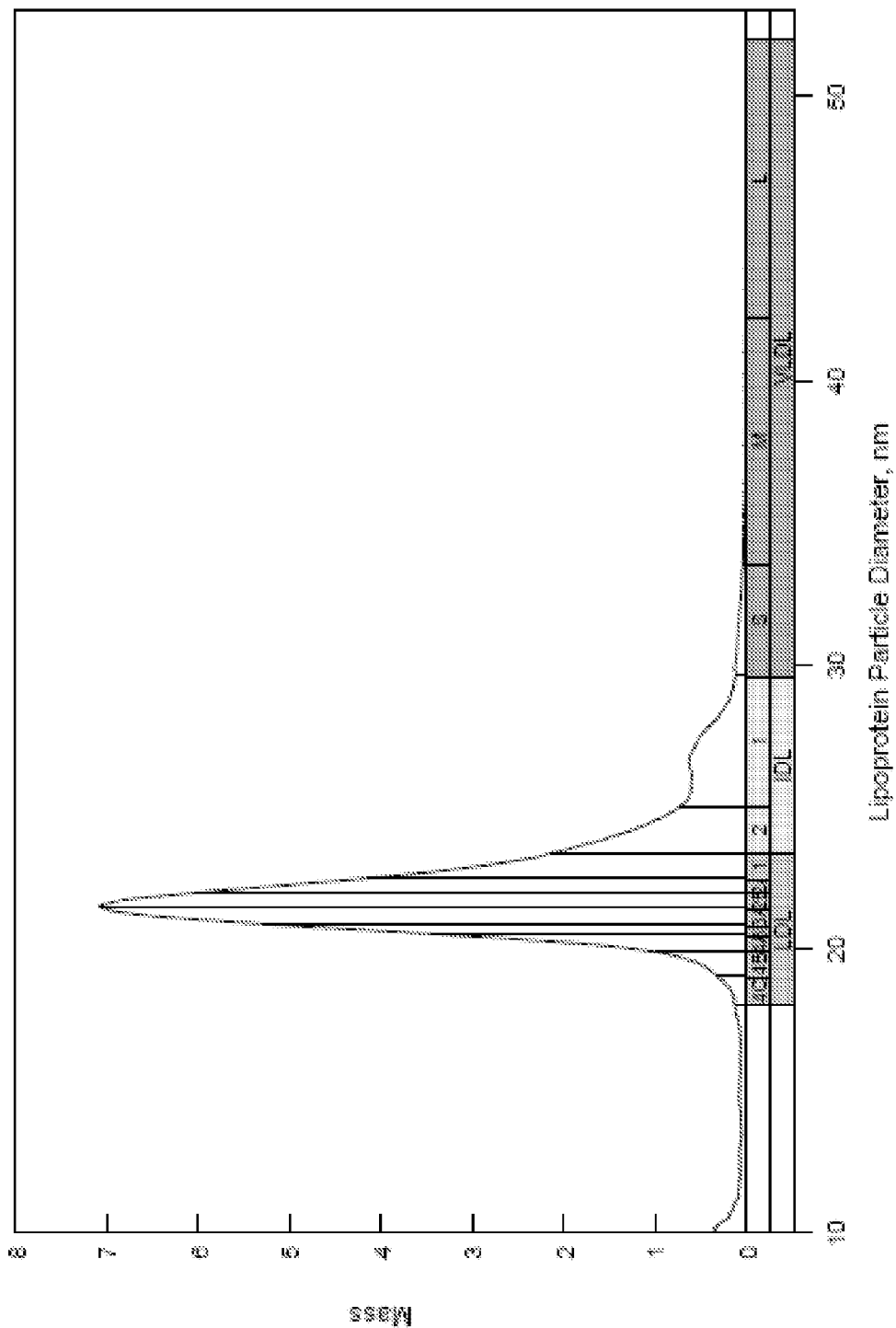
FIG. 8 shows the profile of FIG. 7, converted to mass units, overlaid on a lipoprotein size categorization scheme.

FIG. 7 demonstrates a particle number versus size profile generated from a sample of the Alexa Fluor 488 labeled particles. FIG. 8 shows the particle number profile converted to mass units overlaid on a lipoprotein size categorization scheme. As can be seen in these figures, Alexa Fluor 488 labeling does not alter the LDL profile. The particles remain intact and are detected as LDL particles.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms

TABLE 2

Protocol for HDL labeling with Alexa Fluor 488.

| | Incubation Mixtures | | | | | | | |
|---|---|---|---|---|---|---|---|---|
| | Ligand | | | AF488 | | | | Stop |
| HDL Subf. | Stk Co mg/ml | μl | mg | Stk Co mg/ml | μl | mg | Tot. Vol μl | Soln μl |
| T[0-1] | 3.59 | 560 | 2.01 | 10 | 20.104 | 0.2010 | 580 | 40 |
| T[1-3] | 3.18 | 625 | 1.99 | 10 | 19.875 | 0.1988 | 645 | 40 |
| T[3-6] | 6.39 | 785 | 5.02 | 10 | 50.162 | 0.5016 | 835 | 100 |
| | | | | Total | 90.1405 | 0.901405 | | |

1 - Add HDL subfraction to glass vial containing magnetic-stir bar
2 - While stirring at rm. temp., add AF488 volume to ligand slowly.
3 - Incubate mixture for 1 hour w/continuous stirring.
4 - Add Stop Solution (1.5M Tris, pH 8.0). Incubate at room temp 30 min.
5 - Dialyze labeled HDL Subfractions to 20 mM Tris. 150 mM NaCl, 0.27 mM EDTA, pH 8 [in cold box, protect from light] vs. 1 liter overnight, and 2 × 1 L dialysate volume changes.

The fluorescent probe fluorescein-5-EX, succinimidyl ester, obtained from Molecular Probes (Cat # F-6130), was used to label HDL subfractions in the same manner as described above for AF488. The above methods were also used to fluorescently label VLDL and LDL. Additional tests were conducted to fluorescently label a mixture of high molecular weight standards (Pharmacia HMW Standard Mix) containing thyroglobulin, apoferritin, catalase, lactate dehydrogenase, and albumin.

and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the described invention.

Thus, additional embodiments are within the scope of the invention and within the following claims.

What is claimed is:

1. A method for absolute quantitation of a number of lipoprotein particles in a biological sample, said method comprising:
   a) contacting said sample with a first fluorophore labeled entity capable of integrating into a lipoprotein particle of interest in the sample to generate a first fluorescently labeled lipoprotein particle;
   b) introducing the first fluorescently labeled lipoprotein particles to an apparatus for differential-charged particle mobility analysis and fluorescence detection; and
   c) quantitating the number of fluorescently labeled lipoprotein particles in the apparatus;
   wherein said lipoprotein particles are Lipoprotein (a) particles; and said fluorophore labeled entity is an aptamer or antibody capable of specifically binding Apolipoprotein (a).

2. The method of claim 1, wherein said biological sample is selected from the group consisting of whole blood, serum, and plasma.

3. The method of claim 1, wherein said sample comprises one or more lipoprotein particles selected from the group consisting of high density lipoprotein (HDL), low density lipoprotein (LDL), intermediate density lipoprotein (IDL), very low density lipoprotein (VLDL), and oxidized LDL.

4. The method of claim 3, further comprising:
   d) contacting said sample with a second fluorophore labeled entity prior to introduction into the differential mobility analyzer,
   wherein said second fluorophore labeled entity comprises fluorophore labeled aptamers or antibodies capable of specifically binding one or more of Apolipoprotein A1 (Apo A1) or Apolipoprotein B (Apo B), and wherein said first and said second fluorophore labeled entities have different fluorescence characteristics.

5. The method of claim 4, further comprising:
   e) contacting said sample with a third fluorophore labeled entity prior to introduction into the differential mobility analyzer,
   wherein said third fluorophore labeled entity comprises a fluorophore labeled binding protein capable of specifically binding oxidized LDL, and wherein said first, said second, and said third fluorophore labeled entities have different fluorescence characteristics.

6. The method of claim 1, wherein said first fluorophore labeled entity is a lipophilic fluorophore.

7. The method of claim 6, wherein said lipophilic fluorophore is selected from the group consisting of 1,1'-dioctadecyl-3,3,3',3'-tetramethylindocarbocynanine perchlorate (DiI), 3,3'-dioctadecyloxacarbocynanine perchlorate (DiO), 1,1'-dioctadecyl-3,3,3',3'-tetramethylindodicarbocynanine perchlorate (DiD), and 1,1'-dioctadecyl-3,3,3',3'-tetramethylindotricarbocynanine iodide (DiR), Alexa Fluor 488 (carboxylic acid, succinimidyl ester 'mixed isomers'), and fluorescein-5-EX, succinimidyl ester.

8. The method of claim 6, wherein the lipophilic fluorophore is 1,1'-dioctadecyl-3,3,3',3'-tetramethylindocarbocynanine perchlorate (DiI) or Alexa Fluor 488 (carboxylic acid, succinimidyl ester 'mixed isomers').

9. The method of claim 1, wherein the first fluorophore labeled entity is a fluorophore labeled lipid.

10. The method of claim 9, wherein said fluorophore labeled lipid is labeled with a lipophilic fluorophore.

11. The method of claim 10, wherein said lipophilic fluorophore is selected from the group consisting of 1,1'-dioctadecyl-3,3,3',3'-tetramethylindocarbocynanine perchlorate (DiI), 3,3'-dioctadecyloxacarbocynanine perchlorate (DiO), 1,1'-dioctadecyl-3,3,3',3'-tetramethylindodicarbocynanine perchlorate (DiD), and 1,1'-dioctadecyl-3,3,3',3'-tetramethylindotricarbocynanine iodide (DiR), Alexa Fluor 488 (carboxylic acid, succinimidyl ester 'mixed isomers'), and fluorescein-5-EX, succinimidyl ester.

12. The method of claim 11, wherein the lipophilic fluorophore is 1,1'-dioctadecyl-3,3,3',3'-tetramethylindocarbocynanine perchlorate (DiI) or Alexa Fluor 488 (carboxylic acid, succinimidyl ester 'mixed isomers').

* * * * *